US008577622B2

(12) United States Patent
Hoehne et al.

(10) Patent No.: US 8,577,622 B2
(45) Date of Patent: Nov. 5, 2013

(54) PROCESS FOR THE IDENTIFICATION AND PREPARATION OF A (R)-SPECIFIC OMEGA-TRANSAMINASE

(75) Inventors: Matthias Hoehne, Bruenzow (DE); Uwe Bornscheuer, Greifswald (DE); Karen Robins, Visp (CH); Sebastian Schaetzle, Greifswald (DE)

(73) Assignee: Lonza AG, Visp (CH)

( * ) Notice: Subject to any disclaimer, the term of this patent is extended or adjusted under 35 U.S.C. 154(b) by 0 days.

(21) Appl. No.: 13/393,201

(22) PCT Filed: Aug. 13, 2010

(86) PCT No.: PCT/EP2010/004961
§ 371 (c)(1),
(2), (4) Date: Feb. 28, 2012

(87) PCT Pub. No.: WO2011/026556
PCT Pub. Date: Mar. 10, 2011

(65) Prior Publication Data

US 2012/0156706 A1 Jun. 21, 2012

(30) Foreign Application Priority Data

Sep. 2, 2009 (EP) .................................... 09011271
May 19, 2010 (EP) .................................... 10005203

(51) Int. Cl.
*G06F 19/22* (2011.01)
*C12N 9/10* (2006.01)

(52) U.S. Cl.
USPC ............... 702/19; 530/350; 435/16; 435/128; 435/193

(58) Field of Classification Search
None
See application file for complete search history.

(56) References Cited

FOREIGN PATENT DOCUMENTS

| | | | |
|---|---|---|---|
| CN | 101384723 | A | 3/2009 |
| EP | 0 987 332 | A1 | 3/2000 |
| WO | WO 03/068909 | A2 | 8/2003 |
| WO | WO 2007/093372 | A1 | 8/2007 |

OTHER PUBLICATIONS

Birren, B., et al., "SubName: Full=Putative uncharacterized protein," UNIPROT, 1 pg. (Oct. 17, 2006).

Iwasaki, A., et al., "Microbial synthesis of chiral amines by (*R*)-specific transamination with *Arthrobacter* sp. KNK168," *Applied Microbiology and Biotechnology*, vol. 69(5), pp. 499-505 (Jan. 1, 2006).

Kim, J., et al., "Cloning and Characterization of a Novel β-Transaminase from *Mesorhizobium* sp. Strain LUK: a New Biocatalyst for the Synthesis of Enantiomerically Pure β-Amino Acids," *Applied and Environmental Microbiology*, vol. 73(6), pp. 1772-1782 (Mar. 1, 2007).

Stirling, D., et al., "The Use of Aminotransferases for the Production of Chiral Amino Acids and Amines," *Chirality in Industry: The Commercial Manufacture and Applications of Optically Active Compounds*, pp. 209-222 (Jan. 1, 1992).

Sullivan, J., et al., "SubName: Full=Putative Branched-Chain Amino Acid Aminotransferase Protein," UNIPROT, 1 pg. (Oct. 1, 2002).

GenPept Accession No. XP_001209325; version XP_001209325.1 GI:115385557; "conserved hypothetical protein [*Aspergillus terreus* NIH2624]", Mar. 31, 2008 (2 pages).

GenBank Accession No. CAD31279; version CAD31279.1 GI:20804076; "putative branched-chain amino acid aminotransferase protein [*Mesorhizobium loti* R7A]," Apr. 16, 2005 (2 pages).

Office Action from Chinese Application No. 201080039297.2, dated Jan. 14, 2013. *English translation included* (19 pages).

*Primary Examiner* — Michael Borin

(74) *Attorney, Agent, or Firm* — Kilpatrick Townsend & Stockton LLP

(57) ABSTRACT

The present invention relates to processes for the screening, preparation and characterization of (R)-selective ω-transaminases, to transaminases obtained thereby and their uses in various transamination processes.

8 Claims, 5 Drawing Sheets

Figure 1 – B3APi standard
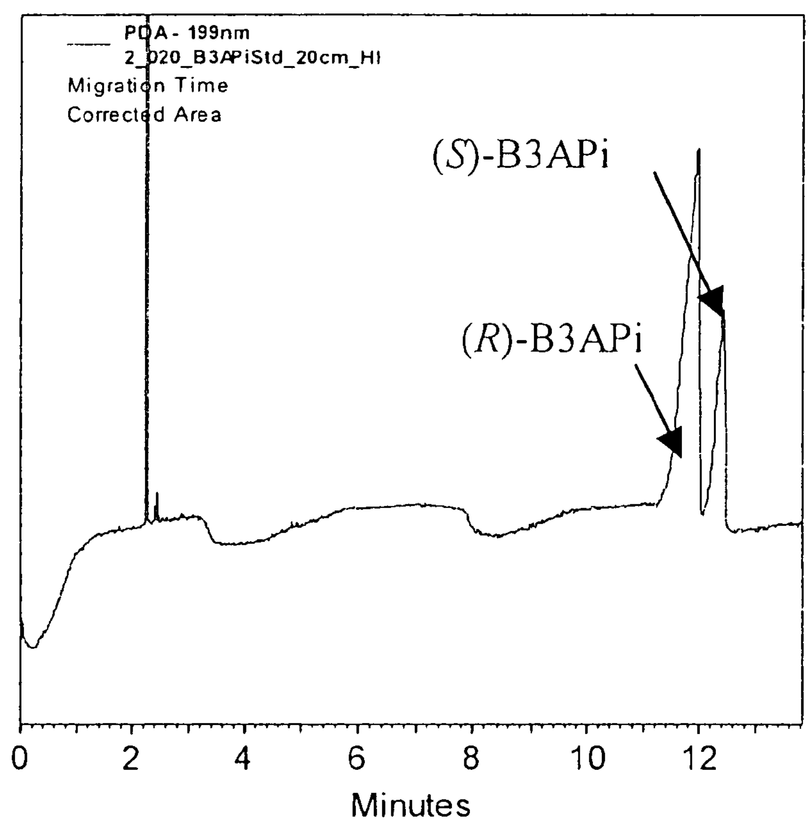

Figure 2 – B3APi asymmetric synthesis
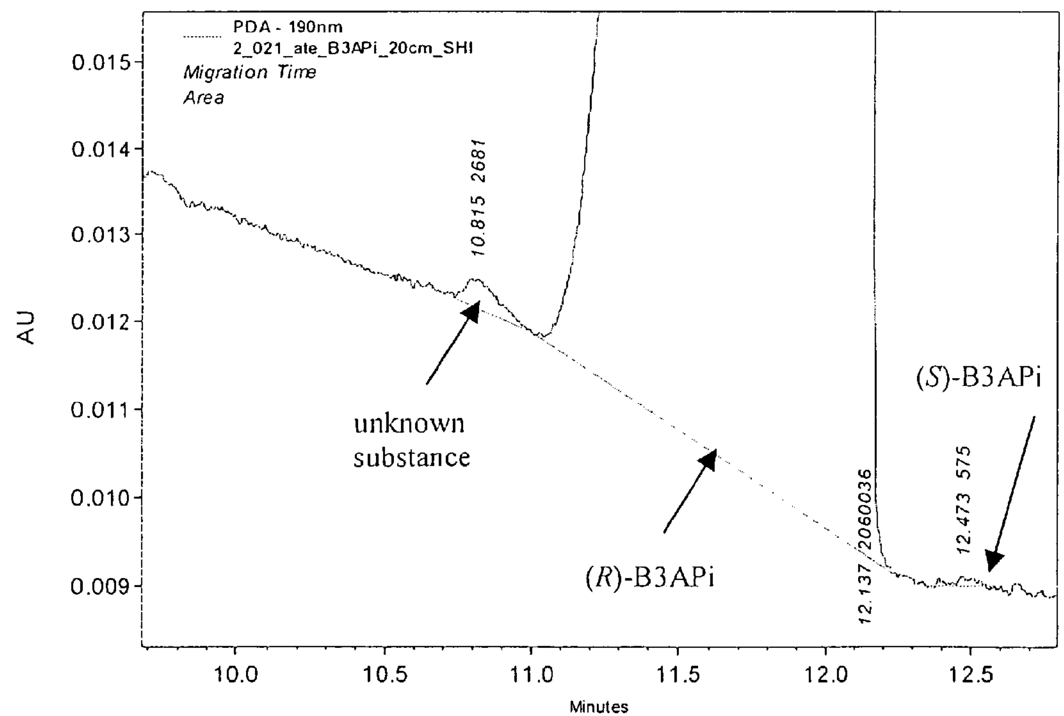

Figure 3 – asymmetric synthesis of C3AP
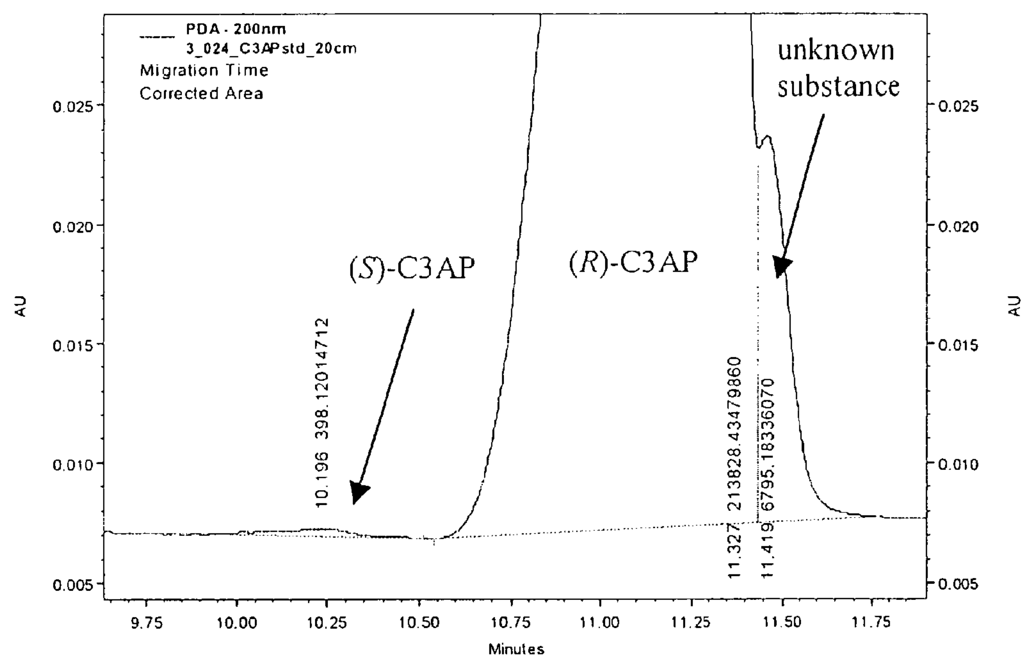

Figure 4 – asymmetric synthesis of MPPA
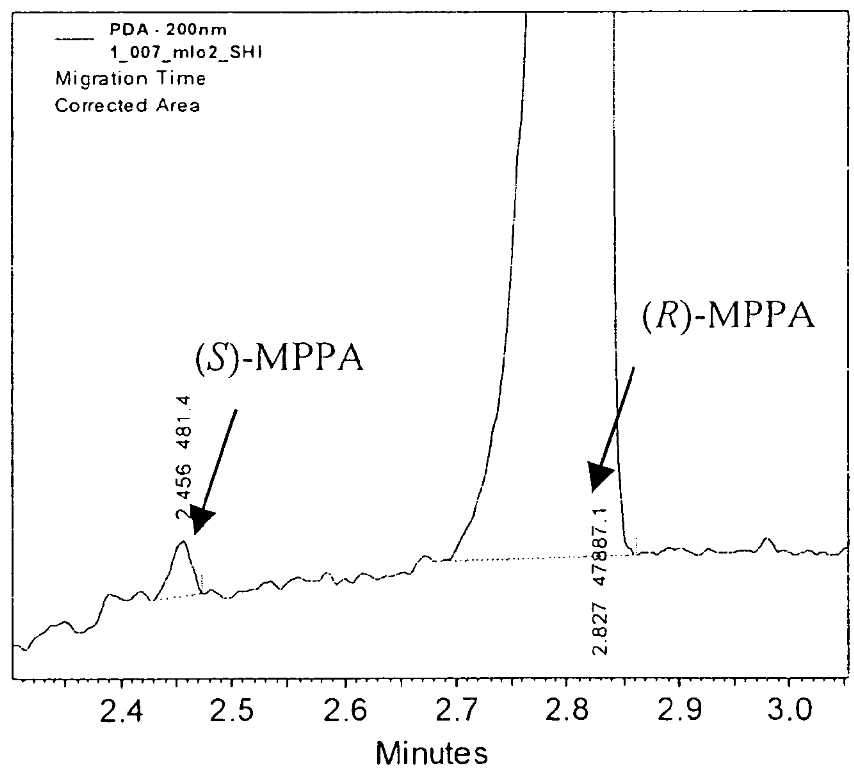

Figure 5 – asymmetric synthesis of B3AP
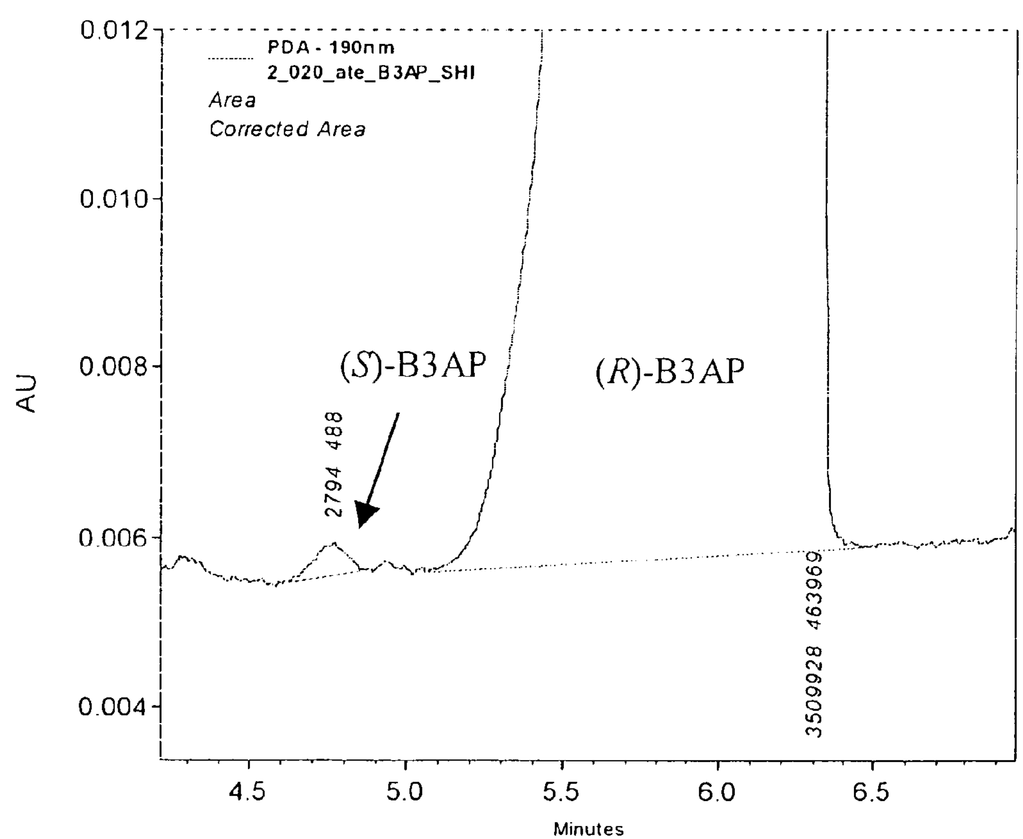

PROCESS FOR THE IDENTIFICATION AND PREPARATION OF A (R)-SPECIFIC OMEGA-TRANSAMINASE

CROSS-REFERENCE TO RELATED PATENT APPLICATIONS

The present application is a U.S. National Phase of PCT/EP2010/004961, filed Aug. 13, 2010, which claims benefit of European Application No. 09011271.5, filed Sep. 2, 2009, and European Application No. 10005203.4, filed May 19, 2010, the entire contents of which are incorporated by reference herein in their entirety.

REFERENCE TO SEQUENCE LISTING

This application includes a Sequence Listing as a text file named "SEQTXT_93638-000600U.S. Pat. No. 830228.txt" created Feb. 14, 2012, and containing 96,384 bytes. The material contained in this text file is incorporated by reference in its entirety for all purposes.

The present invention relates to processes for screening, characterization and preparation of (R)-specific ω-transaminases, to the ω-transaminases obtained thereby and their use in various transamination processes.

Chiral amines play an important role in the pharmaceutical, agrochemical and chemical industry. They are frequently used as intermediates or synthones for the preparation of various physiologically, for instance pharmaceutically active substances, such as cephalosporine or pyrrolidine derivatives. In a great number of the various applications of chiral amines, only one particular optically active form, either the (R) or the (S) enantiomer is physiologically active. There is accordingly a need to provide processes for the preparation of chiral amines in an optically active form.

These needs are partially met by preparing chiral amines by crystallisation of diastereomeric salts through adding of chiral carboxylic acids (Breuer et al., Angewandte Chemie (2004) 116, 806-843). Other chemical methods use enantioselective synthesis by reducing prochiral precursors with C═N-double bonds.

Among several enzymatic methods that have been employed for the synthesis of optically active amino acids and amines, ω-transaminases (ω-TAs) have recently received increased attention, because of their potential for the asymmetric synthesis of optically active amines, which are frequently used as building blocks for the preparation of numerous pharmaceuticals.

ω-transaminases are PLP (pyridoxal phosphate) dependent enzymes that catalyze amino group transfer reactions. When employing ω-transaminases, so-called enantioenriched and/or pure optically active amines can principally be produced via two reaction strategies (i) the asymmetric synthesis starting from ketones, and (ii) the kinetic resolution starting from racemic amines. Although ω-transaminases exhibit good enantioselectivity in general, they have not been used frequently in asymmetric synthesis, although in this case a 100% yield is theoretically possible. One specific requirement in an asymmetric synthesis employing ω-transaminases is to shift the equilibrium to the product side, especially when using an amino acid like alanine as amino donor, since in this case the equilibrium is on the side of the substrates (ketone, alanine) and not on the side of the products (amine, pyruvate); another requirement is that the stereoselectivity of the enzyme has to be perfect, which is not always the case for ω-transaminases. Therefore, ω-transaminases are mainly used for the kinetic resolution of racemic amines, where enantioselectivity does not necessarily need to be perfect. Thus, although kinetic resolutions of racemic amines have been investigated, the limitation to a maximum yield of 50% considerably hampers their application. On the other hand, asymmetric synthesis requires methods to shift the unfavourable equilibrium towards synthesis of single enantiomers of optically pure amines for which several methods were developed, which is one key prerequisite for efficient processes to enable the use of transaminases in industrial scale. Such methods are disclosed in WO 2007/093372.

EP 0 987 332 A1 discloses a process for producing optically active amino compounds, namely (R)-amino compounds, by means of a microbial enzyme, in particular a (R)-selective ω-transaminase derived from *Arthrobacter* sp. EP 1 038 953 A1 discloses a further (R)-selective ω-transaminase, which, however, is derived from *Mycobacterium aurum*.

Iwasaki et al. (Biotechnol. Let. 2003 (25), 1843-1846), Koszelewski et al. (Adv. Synth. Catal. 2008 (350), 2761-2766) and Iwasaki et al. (Appl. Microbiol. Biotechnol. 2006 (69), 499-505) disclose a R-specific transaminase from *Arthrobacter* sp. The identification of microorganism providing useful (S)- or (R)-selective transaminases is usually done by selecting microorganism obtained from for instance soil samples and enriching them in culture (Jun et al., App. Microbiol. Biotechnol. 2004 (70), 2529-2534 and Shin et al. (Biosc. Biotechnol. Biochem. 2001 (65), 1782-1788)). Especially all described R-selective ω-transaminases were obtained by enrichment culture. Such methods are time-consuming, since for an efficient process it is often preferred to overexpress the enzyme in a heterolougeous or ganism like *Escherichia coli*. This requires the isolation of the gene sequence from the wild type organisms but the cloning of the DNA sequence is not always successful and a very time-consuming process.

In particular, during process development or for the identification of novel ω-TA, purification of the enzyme and characterization of their enzymatic properties is of great interest. Since, however, the ω-TA activity is usually determined with low throughput methods like HPLC or capillary electrophoresis (CE), the determination of the enzyme properties is rather often the limiting step.

In general in comparison to (S)-selective ω-transaminases the number of available (R)-selective ω-transaminase is much more limited. This stands in sharp contrast to the high demand for (R)-selective ω-transaminases which are highly desirable for the asymmetric synthesis of (R)-enantiomers of various chiral-amines. Thus, there is still the need to provide further (R)-selective transaminases and means and methods to obtain them in order to produce R-enantiomers, in particular optically active amines, for instance for pharmaceutical or agrochemical applications, which are up to now either not available at all or not in an economically feasible process, preferably in industrial scale.

The present invention is therefore based on the technical problem to provide simple, fast and reliable means and methods to identify, characterize and obtain (R)-selective ω-transaminases, in particular for the production of desired (R)-enantiomers, preferably in optically pure form, which are preferably suitable for identification, characterization and preparation in an industrial scale.

The present invention solves its technical problem by the provision of the teaching of the independent claims, in particular the claimed process, the products and uses obtained thereby.

Thus, the present teaching provides in a particular embodiment a process for the preparation of a (R)-selective ω-transaminase (also called ω-TA), comprising the following steps:

a) providing at least one query biomolecule sequence of at least one transaminase or lyase, preferably a transaminase or lyase which belongs to fold-type IV of PLP-dependent enzymes, and at least one biomolecule bank, b) searching the biomolecule bank with the query biomolecule sequence to identify a group of first target bio-molecule sequences, wherein the first target biomolecule sequences have a degree of sequence identity of at least 20%, preferably 32%, to the query biomolecule sequence, calculated on amino acid level, c) selecting in the group of first target biomolecule sequences a group of second biomolecule target sequences, which do not comprise, on amino acid level, at least one of the following amino acid sequence motives c1) to c3) with c1) at position 95 to 97 an amino acid sequence Tyr Xa1 Xa2, with Xa1 being an amino acid Ile, Val, Leu, Met, Phe, and Xa2 being an amino acid Arg or Lys or c2) at position 97 to 99 an amino acid sequence Tyr Xaa Gln, with Xaa being an amino acid, preferably a conventional amino acid and in the region from position 105 to 111, preferably at position 107 to 109, an amino acid sequence Arg Xaa Xa3, Xa3 being an amino acid, preferably being His or c3) at position 38 Thr, at position 97 Lys and at position 107 to 109 an amino acid sequence Arg Xa4 Xa5, Xa4 being an amino acid, preferably being Gly, and Xa5 being an amino acid, preferably being Tyr, and which comprise c4) at position 95 another amino acid than Tyr, Arg, Lys, or at position 95 Tyr, but at position 97 no Arg or Lys and c5) at position 40 no Lys or Arg and c6) in the region from position 161 to 165, preferably at position 163, Lys to identify a group of second target biomolecule sequences and d) providing, preferably preparing, a biomolecule having the second biomolecule target sequence identified in step c) and being or coding at least partially a protein with the activity of a (R)-selective ω-transaminase.

The term "a biomolecule being or coding at least partially a protein" means preferably that the biomolecule may either be a protein with the activity of a (R)-selective ω-transaminase or, in case the bio-molecule is a nucleotide sequence, at least a part of said nucleotide sequence codes said protein, preferably a full-length protein. Accordingly, in case the provided biomolecule is a nucleotide sequence molecule, at least a part of said nucleotide sequence molecule codes a protein with the activity of a (R)-selective ω-transaminase, whereby possibly a further part of said nucleotide molecule has some other function, for instance regulatory or replicative function. Thus, the term "providing a biomolecule having the second biomolecule target sequence identified in step c) and being or coding at least partially a protein with the activity of a (R)-selective ω-transaminase" is preferably equivalent to the term "providing a biomolecule having the second biomolecule target sequence identified in step c) which may be a protein with the activity of a (R)-selective ω-transaminase or which may be a nucleotide sequence molecule which includes a sequence coding said protein as long as the protein has the activity of a (R)-selective ω-transaminase".

In one embodiment of the present invention in step c2) the position of the Arg Xaa Xa3-motive may vary by 1-2 amino acids from positions 107 to 109, i.e. may be at positions 105 to 111.

In one embodiment of the present invention in step c6) the position of Lys may vary by 1-2 amino acids at position 163, i.e. may be at positions 161 to 165.

In the context of the present invention each amino acid sequence, in particular amino acid sequence motive, or DNA sequence or DNA sequence motive given is given in the amino terminal to carboxy terminal or 5' to 3' direction, whichever applies, and unless otherwise specified. Preferably, the sequences given in the given direction are given as a continuous stretch without any intervening nucleotides or amino acids, whichever applies.

In a preferred embodiment of the present invention the at least one query biomolecule sequence of at least one transaminase as used in step a) is preferably a (R)-selective ω-transaminase. In a further preferred embodiment the at least one query biomolecule sequence of the at least one transaminase as used in step a) is selected from the group consisting of a (R)-selective ω-transaminase, a branched chain amino acid amino transferase (BCAT) and a D-amino acid transaminase (DATA). Preferably, the branched chain amino acid amino transferase is from *E. coli*. In a preferred embodiment of the present invention the at least one query biomolecule sequence of the at least one lyase as used in step a) is an amino deoxychorismatlyase (ADCL).

The present invention provides a process for the preparation of a (R)-selective ω-transaminase in a fast, efficient, simple, reliable and easy manner. The present invention therefore allows to identify and prepare (R)-selective ω-transaminase, which have not been known or accessible before, opening up numerous ways to provide chiral amines, preferably (R)-enantiomers, in particular in very efficient asymmetric synthesis routes. It could be successfully shown that even proteins with a low degree of sequence identity, for instance only 35%, to known (R)-selective ω-transaminase in contrast to the expectations are in fact (R)-selective ω-transaminases. In a particularly advantageous and unexpected manner the present invention allows preferably to provide (R)-selective ω-transaminases from *Aspergillus terreus* and *Mesorhizobium loti*, whereby the transaminase from *Aspergillus* is the first eucaryotic ω-transaminase and it converts substrates with (R)-selectivity.

Basically, the present invention is based on the technical teaching that proteins or its encoding nucleotide sequences, even with a low degree of sequence identity to known transaminases or lyases, in particular (R)-selective ω-transaminases, can be used as a potential source for identifying and preparing (R)-selective ω-transaminases, whereby the putative (R)-selective ω-transaminases are screened and prepared by discriminating undesired and thereby positively selecting for proteins displaying particular sequence motives in the amino acid sequence, which attribute to the desired enzymatic activity. Thus, the present invention specifically uses particular structural features, in particular the absence and presence of particularly amino acids in putative (R)-selective ω-TA, to identify and prepare (R)-selective ω-transaminases.

Accordingly, in a first step a) of the present process, a query bio-molecule sequence of at least one transaminase or lyase, for instance a known (R)-selective ω-transaminase, or at least a characteristic sequence part for such a lyase or transaminase, preferably of the (R)-specific ω-transaminase, which preferably is in particular able to identify a PLP-dependent enzyme of fold type IV, is provided together with at least one biomolecule bank. Preferably, the query biomolecule sequence is an ORF (open reading frame) of a transaminase or lyase, in particular of the (R)-selective ω-TA, coding nucleotide sequence, or a characteristic part thereof. In another embodiment the query biomolecule sequence is the ORF-amino acid sequence itself or a characteristic part thereof.

In the context of the present invention a characteristic part of the query biomolecule sequence of at least one transaminase or lyase, in particular of the known (R)-selective ω-transaminase, is a bio-molecule sequence which in form of its DNA sequence molecule hybridises under the following conditions to the full length query bio-molecule sequence, in particular to the DNA sequence of the ORF.

Methods for the hybridization of nucleic acids such as DNA are well known and are described for example in Molecular Cloning, Third Edition (2001); Methods for General and Molecular Bacteriology, ASM Press (1994); Immunology methods manual, Academic Press (Molecular), and many other standard textbooks.

An example for a hybridization under stringent conditions is as follows. A filter with a nucleic acid immobilized thereon and the nucleic acid used as probe are incubated in a solution comprising 50% formamide, 5×SSC (750 mM sodium chloride and 75 mM sodium citrate), 50 mM sodium phosphate (pH 7.6), 5×Denhardt's solution, 10% dextran sulfate and 20 μg/l denatured salmon sperm DNA at 42° C. overnight. After incubation, the filter is washed in 0.2×SSC solution (ca. 65° C.). These stringent hybridizations conditions can be modified by adjusting the concentration of formamide (the conditions become less stringent as the concentration of formamide is lowered) and by changing the salt concentrations and the temperature conditions.

Hybridization under less stringent conditions is carried out, for example, by incubating a filter with a nucleic acid immobilized thereon and a nucleic acid used as probe in a solution comprising 6×SSCE (20×SSCE: 3 mol/l sodium chloride, 0.2 mol/l sodium dihydrogenphosphate and 0.02 mol/l EDTA, pH 7.4), 0.5% SDS, 30% form amide and 100 μg/l denatured salmon sperm DNA at 37° C. overnight, and washing the filter with 1×SSC solution containing 0.1% SDS (50° C.).

In a particularly preferred embodiment the present invention understands under the term "at least one query biomolecule sequence of at least one transaminase or lyase" a biomolecule sequence, which is suitable to select for biomolecule sequences in accordance with the presence or absence of sequence motives c1) to c6) as identified herein. Accordingly, such a query biomolecule sequence is a sequence screening for and identifying those biomolecule sequences which do not comprise on amino acid level at least one of the amino acid sequence motives c1) to c3) and which comprise on amino acid level sequence motives c4), c5) and c6). Such a query biomolecule sequence may be embodied as an amino acid sequence information or as a DNA sequence molecule or DNA sequence information.

In a preferred embodiment the characteristic part of the query bio-molecule sequence used in step a) encompasses, preferably consists of, the region from positions 30 to 170, most preferably 30 to 120 of the ORF of a transaminase, preferably a (R)-selective ω-transaminase, or a lyase.

The biomolecule bank is in a subsequent step b) searched with the query biomolecule sequence to identify a group of first target bio-molecule sequences, which show at least a minimum degree of sequence identity of at least 20%, preferably 25%, preferably 32%, preferably at least 33%, most preferably 34%, at least 35%, at least 36%, at least 40%, at least 50%, at least 60%, at least 70% and at least 80%, at least 90% or at least 95% to the query biomolecule sequence, based on amino acid level, and wherein said group of first target biomolecules represents a first selection from the biomolecule bank used in step a). Said degree of sequence identity is preferably a sequence identity between at least the characteristic part of the, preferably essentially the complete, in particular the complete, ORF of the query biomolecule sequence and at least the characteristic part of the, preferably essentially the complete, in particular the complete ORF of the biomolecule sequences screened. Subsequent to said step b) in this group of first target biomolecule sequences, those sequences are selected in a step c), which do not comprise as a sequence motive c1) at position 95 to 97 an amino acid sequence Tyr Xa1 Xa2, with Xa1 being an amino acid Ile, Val, Leu, Met, Phe, and Xa2 being an amino acid Arg or Lys or which do not comprise as sequence motive c2) at position 97 to 99 an amino acid sequence Tyr Xaa Gln, with Xaa being an amino acid, preferably a usual amino acid, and in the region from position 105 to 111, preferably at position 107 to 109, an amino acid sequence Arg Xaa Xa3, Xa3 being an amino acid, preferably an usual amino acid, preferably being His or which do not comprise sequence motive c3) at position 38 Thr, at position 97 Lys and at position 107 to 109 an amino acid sequence Arg Xa4 Xa5, Xa4 being an amino acid, preferably an usual amino acid, preferably being Gly, and Xa5 being an amino acid, preferably an usual amino acid, preferably being Tyr, thereby discriminating and discharging those sequences, which do display at least one of the above-identified sequence motives c1), c2) or c3). In a further subsequent or simultaneous selection those biomolecule sequences are selected, which according to sequence motive c4) do show at position 95 another amino acid than Tyr, Arg, Lys, or at position 95 Tyr, but at position 97 no Arg and no Lys and which according to sequence motive c5) have at position 40 no Lys and no Arg and which according to sequence motive c6) have in the region from position 161 to 165 at least one Lys, preferably one Lys, preferably at position 163 Lys, so as thereby to select and identify a group of second biomolecule target sequences. The group of second target bio-molecule sequences identified and screened for the above-identified sequence motives represent biomolecule sequences being or encoding a protein with the activity of an (R)-selective ω-transaminase, which is provided thereby.

In the context of the present invention, a transaminase is a pyridoxalphosphate-dependent enzyme catalysing the transfer of amino groups, being preferably classified in folding type IV. Transaminases are classified in E.C. 2.6.1.X. In a particularly preferred embodiment of the present invention, the transaminase is a (R)-selective transaminase, particular is in a preferred embodiment an ω-transaminase. In the context of the present invention a protein with the activity of an (R)-selective ω-transaminase is a protein which is able under appropriate reaction conditions to catalyse a transfer of nitrogenous groups such as amino groups from the donor to an acceptor such as a (R)-selective ω(omega)-transaminase (beta-alanine-pyruvate transaminase) is able to do so. In context of the present invention a (R)-selective ω-transaminase is preferably an enzyme with the classification code E.C.2.6.1.18.

In the context of the present invention the term optically active chiral amine relates to the same subject-matter as the term enantiomerically active chiral amine. These terms in particular refer to a preparation which is essentially free, in an even more preferred embodiment free of the undesired enantiomer. Accordingly, an optically active chiral amine essentially comprises an excess of one enantiomer or even consists of only one enantiomer.

In particular, in the context of the present invention, an optically active chiral amine has an optical purity of at least 70, 80, 90, 91, 92, 93, 94, 95, 96, 97, 98, 99, 99.5, 99.6, 99.7, 99.8 and in particular at least 99.9%.

In the present invention the optical purity is given in % excess of one enantiomer over the other enantiomer. Thus, the optical purity in % is the quotient of the difference between the (R) and the (S) enantiomer concentrations and the sum of the concentrations of both enantiomers (optical purity of A in %=([A]−[B]):([A]+[B])×100, wherein A and B represent the concentrations of the (R) and (S) enantiomers or vice versa).

In the context of the present invention a biomolecule bank is a source of biomolecules itself or a collection of sequence data of biomolecules, in particular polynucleotide or polypeptide sequence data.

In the context of the present invention a biomolecule is preferably a polynucleotide molecule carrying genetic information, in particular a DNA molecule. In a further preferred embodiment of the present invention a biomolecule is a polypeptide, in particular protein, comprising a number of amino acids. Thus, a biomolecule bank may either be a physical source of biomolecules, in particular may be a gene bank, in particular a cDNA- or genomic library or is a collection of information about said biomolecules, in particular a collection of sequence data, in particular amino acid sequences or polynucleotide sequence, in particular DNA sequences.

The present invention refers also to biomolecule sequences, amino acid sequences, polynucleotide sequences or nucleotide sequences, in particular DNA sequences, whereby said wording designated on one hand the physical substance per se, that means a protein, a polypeptide or a DNA molecule, and on the other hand the information content of said chemical substance, which, in case a polynucleotide is referred to is the type, order and number of its nucleotides and, in case a polypeptide is referred to, is the type, order and number of the single amino acids forming the polypeptide.

In the context of the present invention the terms “biomolecule”, “DNA molecule”, “polynucleotide molecule”, “polypeptide” or “protein” refers to chemical substances per se. In case, the present invention specifically refers to an amino acid sequence information, a DNA sequence information, a polynucleotide sequence information or a biomolecule sequence information, it is referred not to the physical form of a biomolecule, but rather to the information contained therein, i.e. the type, order and number of its constituents, namely the amino acids or nucleotides.

The present invention is, in one preferred embodiment A), in its steps a) to c) applicable to a biomolecule bank being a collection of sequence data of, in one embodiment, polynucleotide sequences, in particular DNA sequences or, in another embodiment, amino acid sequences, both of which are searched in a step b) with sequence alignment tools, preferably such as BLAST, which is a basic local alignment search tool, to identify a group of first target biomolecule sequences (Altschul, S. F. et al. 1990. J. Mol. Biol. 215:403; Altschul, S. F. et al. 1997. Nucleic Acid Res. 25:3389-3402). Other suitable programs include GAP, BESTFIT and FASTA in the Wisconsin Genetics Software Package (Genetics Computer Group (GCG), Madison, Wis., USA). In a further step c) the group of identified first bio-molecule sequences is subjected to further selection steps in the course of which the identified sequence motives are used to identify and select negatively with sequence motives c1) to c3) and select positively with sequence motives c4) to c6) the desired biomolecule sequence. Once the second group of biomolecule sequences is identified, the present invention uses said sequence information to prepare corresponding oligo- or polynucleotide molecules, for instance hybridisation primers, to screen and select in physical forms of biomolecule banks DNA sequence molecules encoding the enzymes identified in the second group. Thus, in a preferred embodiment the sequence information obtained in step c) can be used for cloning of a corresponding gene from a genomic DNA or cDNA library and expression of the protein in, for instance *E. coli, Saccharomyces cerevisiae, Pichia pastoris* or others. In another preferred embodiment of the present invention the sequence information obtained in step c) is used to de novo synthesize the desired (R)-selective ω-transaminase. In such a preferred embodiment it is possible to use the sequence information obtained in step c) for the synthesis of a gene, with for instance an optimized codon usage and mRNA stability, and cloning and expression of such a gene. According to such a preferred embodiment it is possible to use as the at least one biomolecule bank in step a) either a biomolecule bank containing DNA sequence information or amino acid sequence information. In case, the biomolecule bank contains DNA sequence information said information either has to be translated into amino acid sequence information in order to be processed according to steps b) to c), in which amino acid sequences are used as a query bio-molecule sequence and as amino acid sequence motives or steps b) to c), which are carried out in the DNA sequence bank using query bio-molecule sequences and sequence motives c1) to c6) translated back into DNA sequence information.

In another preferred embodiment of the present invention the present teaching is applied in an embodiment B) in step a) to a bio-molecule bank which is present in physical form of a gene bank, in particular gene library such as a cDNA-, metagenome or genomic library, using DNA molecules encoding all or at least the characteristic part of at least one (R)-selective ω-transaminase, to search for, identify and select a group of first biomolecule sequences, in particular DNA sequence molecules, which, calculated on amino acid level, have a degree of sequence identity of at least 20%, preferably 32% to the query DNA sequence molecule. The subsequent step c) is preferably carried out in said group of first DNA molecules using nucleotide molecule primers identifying and positively and negatively selecting for the desired sequence motives c1) to c6).

In the context of the present invention the term “sequence motive” refers to the specific selective characteristics of the amino acid sequence of the putative (R)-selective ω-transaminase as identified specifically in step c) of the claimed process. In particular, the first sequence motive c1) is the sequence motive identified at position 95 to 97 being in this order an amino acid sequence Tyr Xa1 Xa2, with Xa1 being an amino acid Ile, Val, Leu, Met, Phe, and Xa2 being an amino acid Arg or Lys and which should according to the present invention not be present in the finally selected biomolecule sequence. The second sequence motive c2) is the sequence motive identified at position 97 to 99 being in this order an amino acid sequence Tyr Xaa Gln, with Xaa being an amino acid and in the region from position 105 to 111, preferably at position 107 to 109, an amino acid sequence being in this order Arg Xaa Xa3, with Xaa being an amino acid and Xa3 being an amino acid, preferably being His, and which also should not be present in the finally selected biomolecule sequence. The third sequence motive c3) is the sequence motive characterized by the presence of Thr at position 38, at position 97 Lys and at position 107 to 109 an amino acid sequence Arg Xa4 Xa5, Xa4 being an amino acid, preferably being Gly and Xa5 being an amino acid, preferably being Tyr, which motive c3) should not be present in the finally selected biomolecule sequence.

The fourth sequence motive c4) requires that at position 95 another amino acid than Tyr, Arg, Lys, or at position 95 Tyr, but at position 97 no Arg or Lys is present, which qualifies for a putative (R)-selective ω-transaminase prepared according to the present invention. The fifth sequence motive c5) requires that at position 40 no Lys and no Arg is present in the finally prepared and identified putative (R)-selective ω-transaminase. The sixth sequence motive c6) requires that in the region from position 161 to 165 at least one Lys, preferably one Lys, preferably at position 163 Lys, is present in the finally prepared and identified (R)-selective ω-TA.

In the context of the present invention, the identification and location of the amino acid positions is determined as follows. The first target biomolecule sequences are aligned, preferably multiply aligned to each other and the query biomolecule sequence. Alignment can be done with conventional alignment software, such as STRAP, in particular ClustalW, preferably ClustalW3D. In another embodiment it is also possible to align the sequences pairwise, i.e. each first target biomolecule sequence to the query biomolecule sequence. In a preferred embodiment the first target biomolecule sequences are aligned to the BCAT of *E. coli*. In another preferred embodiment the first target biomolecule sequences are aligned to another query bio-molecule sequence used in the present invention, for instance the (R)-selective ω-transaminase.

The annotation of the amino acid positions as given in the present invention is determined by the position of the corresponding sequence motive in the query biomolecule sequence used as the positional standard. Alignment as described above aligns the corresponding amino acid positions of the first target biomolecule sequences to the sequence motives present in the query biomolecule sequence.

As an example, using the BCAT of *E. coli* as standard for the annotation of the position the known *E. coli* BCAT amino acid sequence from position 92 to 100, namely TSAYIRPLI (SEQ ID no. 9) is used to identify positions 95 to 99 in the putative ω-transaminase, which is analysed for the absence of the sequence motives c1), c2), c3) and in the presence of c4). The known amino acid sequence from position 35 to 42, namely VFEGIRCY (SEQ ID no. 10) of the *E. coli* BCAT marks the position of the G at position 38 for sequence motive c3) and c5). The amino acid sequence DVGMGVNP in the *E. coli* BCAT amino acid sequence (SEQ ID no. 11) marks position 104 to 111 for sequence motive c3) at positions 105 to 111. The amino acid sequence PTAAKAGGN from positions 159 to 167 of the known *E. coli* BCAT (SEQ ID no. 12) marks position 163 as being a K for sequence motive c6).

Thus, in a preferred embodiment of the present invention the bio-molecule is a protein and the biomolecule sequence is an amino acid sequence. Accordingly, in one preferred embodiment the bio-molecule bank is a bank, in particular database, which bank is a bank with collected information on various proteins, in particular amino acid sequence information. Preferred data base banks are the NCBI protein data bank, the UniProtKB/SwissProt and the UniProtKB/TrEMBL data bank.

In a preferred embodiment it is also possible that the biomolecule is a DNA molecule and the biomolecule sequence is a DNA sequence. Accordingly, in one preferred embodiment, the biomolecule bank is a bank, in particular database, with collected information on various polynucleotide sequences, in particular DNA sequences.

In a preferred embodiment the present invention uses a process according to the above, wherein the biomolecule bank is a biomolecule database and the biomolecule database is searched in step b) with a biomolecule sequence alignment program, in particular BLAST. In a preferred embodiment it is foreseen that if the biomolecule bank is a biomolecule database, the biomolecule database is searched in step b) with either an amino acid sequence, if the biomolecule database is an amino acid sequence database, or with a DNA sequence, if the biomolecule database is a DNA sequence database.

The invention foresees in step d) finally to provide a biomolecule, preferably a DNA molecule or an amino acid sequence molecule, i.e. protein, either by de novo synthesis of the transaminase or by isolating from a physical gene bank polynucleotides encoding the desired transaminase with the help of primers, being defined on the base of the second biomolecule sequences. The obtained polynucleotides, in particular DNA sequence molecules, are used to be expressed under appropriate conditions in an appropriate culture medium to express the desired transaminase.

The present invention also relates to a process for the screening and identification of a (R)-selective ω-transaminase, comprising the above-identified steps a) to c), in particular providing at least one query biomolecule sequence of at least one (R)-selective ω-transaminase and at least one biomolecule bank, searching the biomolecule bank with the query biomolecule sequence to identify a group of first target biomolecule sequences, wherein the first bio-molecule sequences have a degree of sequence identity of at least 20%, preferably 25%, preferably 32% to the query biomolecule sequence, calculated on amino acid level, selecting in the group of first target biomolecule sequences biomolecule sequences, which do not comprise, on amino acid level, anyone of the sequence motives c1) to c3) with c1) being at position 95 to 97 an amino acid sequence Tyr Xa1 Xa2, with Xa1 being an amino acid Ile, Val, Leu, Met, Phe, and Xa2 being an amino acid Arg or Lys or c2) being at position 97 to 99 an amino acid sequence Tyr Xaa Gln, with Xaa being an amino acid and in the region from position 105 to 111, preferably 107 to 109, an amino acid sequence Arg Xaa Xa3, Xa3 preferably being an amino acid, preferably His or c3) being at position 38 Thr, at position 97 Lys and at position 107 to 109 an amino acid sequence Arg Xa4 Xa5, Xa4 being an amino acid, preferably being Gly, and Xa5 being an amino acid, preferably being Tyr, and which do comprise sequence motives c4), c5) and c6) with c4) being on amino acid level at position 95 another amino acid than Tyr, Arg, Lys, or at position 95 Tyr, but at position 97 no Arg or Lys and c5) being at position 40 no Lys or Arg and c6) being in the region from position 161 to 165, preferably at position 163, Lys to identify a group of second biomolecule sequences, which are biomolecule sequences of a (R)-selective ω-TA.

In a furthermore preferred embodiment of the present invention the present teaching provides (R)-selective ω-transaminases being obtainable according to the preparation processes of the present invention. In particular, the present invention provides proteins and DNA sequences, in particular DNA molecules, encoding said protein from *Mesorhizobium loti* and *Aspergillus terreus* as identified in SEQ ID no. 1 and 2 for *Mesorhizobium loti* and 3 and 4 for *Aspergillus* terreus. The present invention provides in particular and in a most preferred embodiment the teaching that the (R)-selective ω-transaminases obtainable or prepared according to the present invention, for instance those identified in SEQ ID no. 1 and 3, can be used in a transamination reaction, in particular can be used in a process for the preparation of an optically active chiral amine, preferable an (R)-enantiomer of a chiral amine, comprising reacting at least one amino acceptor and at least one amino donor with the (R)-selective ω-transaminase according to the present invention, in particular of SEQ ID no. 1 or 3, and obtaining the optically active chiral amine. In a preferred embodiment the process for the preparation of an optically active chiral amine is an asymmetric synthesis using as a keto-group containing compound preferably a ketone and an amino donor. In another preferred embodiment the preparation method is using a kinetic resolution reaction. With an amino donor being preferably a mixture of racemic amines and an amino acceptor, preferably ketones, as educts.

In the preferred embodiment of the present invention according to which an optically active chiral amine is synthesized by using a (R)-selective ω-transaminase of the present invention in an asymmetric synthesis starting from ketones the preferred degree of conversion into the desired optical active chiral amine, i.e. the (R)-enantiomer is at least 70%, 80%, 90%, 95%, 98%, 99%, 99.5% and most preferably 100%.

In another preferred embodiment according to which the (R)-selective ω-transaminase of the present invention is used in a kinetic resolution reaction starting from racemic amines the preferred degree of conversion into the optically active chiral amine, preferably the (S)-enantiomer, is at least 30, 40, 45, 46, 47, 48, 49, in particular 50%.

The concentrations for analysing the optical purity and the conversion can be determined for instance using HPLC, capillary electrophoresis (CE), gas chromatography (GC) or photo- or fluorimetric methods.

Thus, in a preferred embodiment, the present invention relates to a process for the preparation of an optical active chiral amine, said process comprising reacting an amino acceptor compound comprising a keto group and a racemic mixture of an amine in the presence of a transaminase, in particular a (R)-selective ω-transaminase, preferably according to the present invention, to obtain an (S)-enantiomer of the chiral amine.

In another preferred embodiment of the present invention there is provided a process for the preparation of an optical active chiral amine, in particular an (R)-enantiomer of said amine that process comprising reacting an amino acceptor compound comprising a keto-group and an amino donor in the presence of a (R)-selective ω-transaminase, in particular obtainable according to the present invention, to obtain an (R)-enantiomer of the amine.

In the context of the present invention an amino acceptor is a molecule capable of accepting an amino group transferred from an amino donor by a transaminase, in particular an ω-transaminase. In a particularly preferred embodiment of the present invention the amino acceptor contains a ketone functionality.

In a particularly preferred embodiment of the present invention the amino acceptor is selected from the group consisting of phenylpyruvic acid, a salt thereof, pyruvic acid, a salt thereof, acetophenone, 2-ketoglutarate, 3-oxobutyrate, 2-butanone, 3-oxopyrrolidine (3-OP), 3-pyridylmethylketone (3-PMK), 3-oxobutyric acid ethyl ester (3-OBEE), 3-oxopentanoic acid methyl ester (3-OPME), N-1-boc-oxopiperidinone, N-1-boc-3-oxopyrrolidine (B3OP), 3-oxopiperidine, N-1-boc-3-oxopiperidine (B3OPi), 1-Cbz-3-oxopiperidine (C3OPi), 1-Cbz-3-oxopyrrolidine (C3OP), alkyl-3-oxo-butonoates, methoxyacetone and 1-oxotetralone.

In the context of the present invention an amino donor is a molecule capable of providing an amino group to an amino acceptor using a transaminase, in particular an ω-transaminase. In a particular preferred embodiment the amino donor is an amine or amino acid.

In a particularly preferred embodiment the amino donor is selected from the group consisting of β-alanine, alanine, α-methylbenzylamine (α-MBA), glutamate, phenylalanine, glycin, 3-aminobutyrate, isopropylamine, 2-aminobutane and γ-aminobutyrate or a salt, for instance a chloride, of any one thereof. In a particularly preferred embodiment the obtained ketone product may be phenylpyruvic acid, a salt thereof, pyruvic acid, a salt thereof, glyoxylic acid, a salt thereof, acetophenone, 2-ketoglutarate, acetone, 3-oxobutyrate, 2-butanone, 3-oxopyrrolidine (3-OP), 3-pyridylmethylketone (3-PMK), 3-oxobutyric acid ethyl ester (3-OBEE), 3-oxopentanoic acid methyl ester (3-OPME), N-1-boc-oxopiperidinone and N-1-boc-3-oxopyrrolidine (B3OP) or a salt, for instance a chloride, of any one thereof.

In a further preferred embodiment the present invention relates to a process for the preparation of an optically active chiral amine which is selected from the group of amines having an optically active amino group, in particular amines with alkylgroups, branched alkylgroups or arylalkylgroups. In particular, these amines, in particular mono- or bicyclic amines, are in particular amines of 5 to 6-membered cyclic or S-, O-, or N-substituted heterocyclic hydrocarbons or aromatic amines, in particular alkyl- or alkoxy-substituted aromatic amines. In a preferred embodiment, the obtained chiral amines are selected from the group consisting of phenylalanine, alanine, 3-aminopiperidine, alkyl-3-amino-butanoates, 3-aminopyrrolidine (3-AP), 3-pyridyl-1-ethylamine (3-PEA), N-1-boc-3-aminopyrrolidine (B3AP), N-1-boc-3-aminopiperidine (B3APi), 1-Cbz-3-aminopiperidine (C3APi), 1-Cbz-3-aminopyrrolidine (C3AP), 3-aminobutyric acid ethyl ester (3-ABEE), 3-aminopentanoic acid methyl ester (3-APME), α-methylbenzylamine (α-MBA), 1-aminotetraline, 3,4-dimethoxy phenyl acetone, α-methyl-4-(3-pyridyl)-butanamine, γ-aminobutyrate, glutamate, isopropylamine, β-aminobutyrate, secbutylamine, methoxyisopropylamine, derivatives of 3-aminopyrrolidine, 1-N-Boc-3-aminopiperidine, cephalosporine and derivatives of cephalosporine.

In a particularly preferred embodiment the present invention therefore foresees reacting 3OP with an (R)-selective ω-transaminase and an amino donor to obtain optically active (R)-3AP.

In a further preferred embodiment, the present invention foresees reacting 3-PMK with an (R)-selective ω-transaminase and an amino donor to obtain optically active (R) 3-PEA.

In a further preferred embodiment of the present invention, the invention foresees reacting 3-OBEE with an (R)-selective ω-transaminase and an amino donor to obtain optically active (R) 3-ABEE.

In a further preferred embodiment the invention foresees reacting 3-OPME with an (R)-selective ω-transaminase and an amino donor to obtain optically active (R) 3-APME.

In a further preferred embodiment the invention foresees reacting B3OP with an (R)-selective ω-transaminase and an amino donor to obtain optically active (R)-B3AP.

In a further preferred embodiment, the present invention foresees reacting B3OPi with an (R)-selective ω-transaminase and an amino donor to obtain optically active (R)-B3APi.

In a further preferred embodiment, the invention foresees reacting C3OPi with an (R)-selective ω-transaminase and an amino donor to obtain optically active (R)—C3APi.

In a further preferred embodiment, the invention foresees reacting C3OP with an (R)-selective ω-transaminase and an amino donor to obtain optically active (R)—C3AP.

In a further preferred embodiment of the present invention the invention foresees reacting acetophenone with an (R)-selective ω-transaminase and an amino donor to obtain optically active (R) α-MBA.

In a further preferred embodiment the present invention foresees reacting as an amino acceptor, in particular mono- or bicyclic, oxogroup-containing 5 to 6 membered cyclic or S-, O-, or N-substituted heterocyclic hydrocarbons or aromatics, in particular alkyl- or alkoxy-substituted aromatics with an amino donor and an (R)-selective ω-transaminase to obtain amines, in particular mono- or bicyclic amines, in particular amines of 5 to 6 membered cyclic or S-, O-, or N-substituted heterocyclic hydrocarbons or aromatic amines, in particular alkyl- or alkoxy-substituted aromatic amines, in particular in (R) form.

In a particularly preferred embodiment of the present invention, the amino acceptor and the amino donor are reacted with the transaminase in aqueous medium, for example physiological buffer. In a particularly preferred embodiment the transamination reaction is carried out at a pH in the range from 5 to 9, in particular from 7 to 8.5. In a particular preferred embodiment, the reaction is carried out in a temperature range from 10 to 65° C., preferably 20 to 50° C., in particular 18 to 25° C., preferably room temperature or 34° C. to 39° C., in particular 37° C. In a further preferred embodiment of the present invention the amino acceptor and the amino donor are provided in a molar ratio from 1:1 to 1:5, in particular from 1:1 to 1:2. In a preferred embodiment of the present invention the enzymatic activity may be from 1 to 20.000 μmol/min.

The present invention also relates to a process for the analysis of a transaminase, in particular for the characterization of properties of a transaminase, comprising the following steps:

i. providing a charged amino acceptor, a charged amino donor and a transaminase, preferably a ω-transaminase, most preferably a (R)-selective ω-transaminase obtainable according to the present invention ii. reacting the amino acceptor and the amino donor with the transaminase in a reaction medium, and thereby iii. determining the conductivity of the reaction medium under a first set of reaction conditions and iv. subsequently to step iii) determining the conductivity of the reaction medium under a second set of reaction conditions, so as to obtain at least two conductivity values reflecting the properties of the transaminase.

In the course of a transaminase, preferably ω-TA-catalyzed, reaction of the charged substrates amino donor, preferably an amine, and the amino acceptor, preferably a keto acid, for instance pyruvate, the conductivity decreases since a non-charged ketone and the zwitterionic amino component, preferably amino acid, for instance alanine are formed.

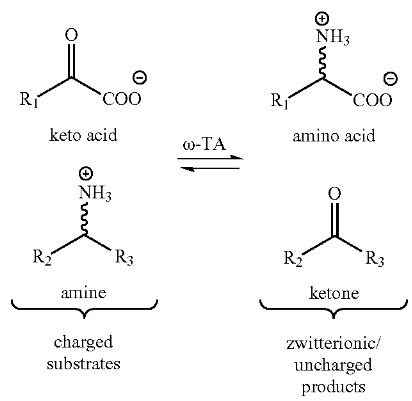

The present process for analysis allows a simple measurement of the reaction progress. Preferably, a low conductivity buffer, particularly the low conducting CHES (N-Cyclohexyl-2-aminoethanesulfonic acid) buffer is most suitable in order to avoid a too high initial conductivity. Preferably, a calibration of the conductivity process can be done by simulation of different conversions. As an example, for the standard substrate pair α-methylbenzylamine and pyruvate, a 1 mM conversion corresponds to a change of 44 μS. A validation of the present process by comparing measured reaction rates with capillary electrophoresis yielded an excellent conformity. Cell extracts do not significantly interfere with the present process. Since pyruvate μs the common amino acceptor of virtually all ω-TA, the present process can be used for investigations of the transaminase activity towards different amino donors. Moreover, also information about enantioselectivity of the enzyme can be obtained.

In this embodiment the invention provides a process for analysing a transaminase, in particular for the characterisation of properties of a transaminase, which allows to analyse the activity of the transaminase in dependency upon for instance the pH-value or the temperature of the reaction medium or allows to analyse the stability of the reaction, the effect of additives or buffer compositions.

According to the present process for analysis a first measurement of the conductivity of the reaction medium is carried out under a first set of reaction conditions and thereafter at least one second measurement of the conductivity of the reaction medium is carried out in order to be able to compare both of the obtained conductivity values and draw conclusions on the activities and properties of the transaminase tested. A decrease in the conductivity shows in a transaminase reaction according to the present invention the activity of said transaminase. Recognising a reduced decrease, an accelerated decrease or no decrease of the conductivity allows drawing conclusions on the properties of the transaminase.

In the context of the present invention a set of reaction conditions is preferably a set of reaction conditions the conditions of which are preferably selected from the group consisting of temperature, pH-value and composition of the reaction medium, preferably reaction conditions as identified above, except the concentration of educts and products. In one embodiment of the present invention the set of reaction conditions are kept constant over the reaction time. In another embodiment of the invention the set of reaction conditions may be different over the reaction time.

In a preferred embodiment, the invention therefore also relates to such a process for the analysis of a transaminase, wherein the reaction medium is a low conductivity buffer. In a particularly preferred embodiment of the process the charged amino acceptor is pyruvate.

In a preferred embodiment of the present invention the present process for the analysis of a transaminase is used subsequently to the process for the preparation of an (R)-selective ω-transaminase of the present invention and extends the teaching of the present invention to not only providing new and advantageous (R)-selective ω-transaminases but also allow to determine their characteristics.

Further preferred embodiments of the present invention are the subject-matter of subclaims.

The present invention is illustrated in more detail in the following examples and the accompanying sequence listing.

SEQ ID no. 1 shows the full amino acid sequence (ORF) of the (R)-selective ω-TA from *Mesorhizobium loti,*

SEQ ID no. 2 shows the DNA-sequence encoding SEQ ID no. 1,

SEQ ID no. 3 shows the full amino acid sequence (ORF) of the (R)-selective ω-TA from *Aspergillus terreus,*

SEQ ID no. 4 shows the DNA sequence encoding SEQ ID no. 3,

SEQ ID no. 5 shows the full amino acid sequence (ORF) of the (R)-selective ω-transaminase from *Mycobacterium aurum,*

SEQ ID no. 6 shows the DNA sequence encoding SEQ ID no. 5,

SEQ ID no. 7 shows the full amino acid sequence (ORF) of the (R)-selective ω-transaminase from *Arthrobacter* sp., SEQ ID no. 8 shows the DNA sequence encoding SEQ ID no. 7, SEQ ID no. 9 shows the sequence motive of *E. coli* BCAT used for determination of positions 95 to 99, SEQ ID no. 10 shows the sequence motive of *E. coli* BCAT used for determination of position 38, SEQ ID no. 11 shows the sequence motive of *E. coli* BCAT used for determination of position 107, SEQ ID no. 12 shows the sequence motive of *E. coli* BCAT used for determination of position 163, SEQ ID no. 13 shows the DNA-sequence encoding the (R)-selective ω-TA from *Penicillium chrysogenum,*

SEQ ID no. 14 shows the full amino acid sequence (ORF) of SEQ ID no. 13,

SEQ ID no. 15 shows the DNA-sequence encoding the (R)-selective ω-TA from *Aspergillus niger,*

SEQ ID no. 16 shows the full amino acid sequence (ORF) of SEQ ID no. 15,

SEQ ID no. 17 shows the DNA-sequence encoding the (R)-selective ω-TA from *Aspergillus oryzae,*

SEQ ID no. 18 shows the full amino acid sequence (ORF) of SEQ ID no. 17,

SEQ ID no. 19 shows the DNA-sequence encoding the (R)-selective ω-TA from *Aspergillus fumigatus,*

SEQ ID no. 20 shows the full amino acid sequence (ORF) of SEQ ID no. 19,

SEQ ID no. 21 shows the DNA-sequence encoding the (R)-selective ω-TA from *Neosartorya fischeri,*

SEQ ID no. 22 shows the full amino acid sequence (ORF) of SEQ ID no. 21,

SEQ ID no. 23 shows the DNA-sequence encoding the (R)-selective ω-TA from *Gibberella zeae,*

SEQ ID no. 24 shows the full amino acid sequence (ORF) of SEQ ID no. 23,

SEQ ID no. 25 shows the DNA-sequence encoding the (R)-selective ω-TA from *Hyphomonas neptunium,*

SEQ ID no. 26 shows the full amino acid sequence (ORF) of SEQ ID no. 25,

SEQ ID no. 27 shows the DNA-sequence encoding the (R)-selective ω-TA from *Mesorhizobium loti* MAFF303099, SEQ ID no. 28 shows the full amino acid sequence (ORF) of SEQ ID no. 27, SEQ ID no. 29 shows the DNA-sequence encoding the (R)-selective ω-TA from *Roseobacter* sp., SEQ ID no. 30 shows the full amino acid sequence (ORF) of SEQ ID no. 29, SEQ ID no. 31 shows the DNA-sequence encoding the (R)-selective ω-TA from *Marinomonas* sp., SEQ ID no. 32 shows the full amino acid sequence (ORF) of SEQ ID no. 31, SEQ ID no. 33 shows the DNA-sequence encoding the (R)-selective ω-TA from *Rhizobium etli,*

SEQ ID no. 34 shows the full amino acid sequence (ORF) of SEQ ID no. 33,

SEQ ID no. 35 shows the DNA-sequence encoding the (R)-selective ω-TA from *Rhodoferax ferrireducens,*

SEQ ID no. 36 shows the full amino acid sequence (ORF) of SEQ ID no. 35,

SEQ ID no. 37 shows the DNA-sequence encoding the (R)-selective ω-TA from *Jannaschia* sp., SEQ ID no. 38 shows the full amino acid sequence (ORF) of SEQ ID no. 37, SEQ ID no. 39 shows the DNA-sequence encoding the (R)-selective ω-TA from *Labrenzia alexandrii,*

SEQ ID no. 40 shows the full amino acid sequence (ORF) of SEQ ID no. 39,

SEQ ID no. 41 shows the DNA-sequence encoding the (R)-selective ω-TA from *Burkholderia* sp., SEQ ID no. 42 shows the full amino acid sequence (ORF) of SEQ ID no. 41, SEQ ID no. 43 shows the DNA-sequence encoding the (R)-selective ω-TA from *Burkholderia cenocepacia,*

SEQ ID no. 44 shows the full amino acid sequence (ORF) of SEQ ID no. 43,

SEQ ID no. 45 shows the DNA-sequence encoding the (R)-selective ω-TA from alpha proteobacterium, SEQ ID no. 46 shows the full amino acid sequence (ORF) of SEQ ID no. 45, SEQ ID no. 47 shows the DNA-sequence encoding the (R)-selective ω-TA from gamma proteobacterium, SEQ ID no. 48 shows the full amino acid sequence (ORF) of SEQ ID no. 47, SEQ ID no. 49 shows the DNA-sequence encoding the (R)-selective ω-TA from *Mycobacterium vanbaalenii* and SEQ ID no. 50 shows the full amino acid sequence (ORF) of SEQ ID no. 49.

FIG. 1 shows a chromatogram of B3APi obtained by a standard synthesis.

FIG. 2 shows a chromatogram of B3APi obtained by the asymmetric synthesis according to the invention.

FIG. 3 shows a chromatogram of C3AP obtained by the asymmetric synthesis according to the invention.

FIG. 4 shows a chromatogram of MPPA obtained by the asymmetric synthesis according to the invention.

FIG. 5 shows a chromatogram of B3AP obtained by the asymmetric synthesis according to the invention.

EXAMPLES

Example 1

Identification of (R)-Selective ω-Transaminases

The amino acid sequence of the (R)-selective ω-TA of *Mycobacterium aurum* as given in EP 1 038 953 A1 (SEQ ID no. 5) and the amino acid sequence of the (R)-selective ω-TA *Arthrobacter* sp. as given in EP 0 987 332 A1 (SEQ ID No. 7) are used as query bio-molecule sequence. The biomolecule bank used in this example is the pubmed protein data bank of the NCBI (http://www.ncbi.nlm.nih.gov/pubmed (13 Jul. 2009).

Using a BLAST search with amino acid sequence from *M. aurum* or *Arthobacter* sp. ω-TA (SEQ ID no. 5 or 7) as query using standard parameters (BLOSUM62 scoring matrix, word size: 3, gap costs: existence—11, extension—1) a first group of 100 various amino acid sequences from different organisms have been identified, which all have a minimum degree of 30% sequence identity to the query sew quence.

For the BLAST the "non-redundant protein sequences (nr)" (http://blast.ncbi.nlm.nih.gov/Blast.cgi?PROGRAM=blastp&BLAST_PROGRAMS=blastp&PAGE_TYPE=BlastSearch&SHOW_DEFAULTS=on&LINK_LOC=blasthome) have been used on 13 Jul. 2009. In this first group of 100 various amino acids representing the first target biomolecule sequences, those sequences have been searched for and identified by a sequence motive search which do not show sequence motives c1), c2) or c3) and which do show sequence motives c4), c5) and c6). 21 ORF could be identified and are listed in Table 1 below.

TABLE 1

| No. | Source Organisms | % Identity with AS-ωTA SEQ ID7 | MA-ω-TA SEQ ID5 | Gene-ident Nr./ Protein-ident. Nr. (NCBI database) |
|---|---|---|---|---|
| 1 | *Aspergillus terreus* NIH2624 | 44 | 40 | 115385557 |
| 2 | *Penicillium chrysogenum* Wisconsin 54-1255 | 44 | 42 | 211591081 |
| 3 | *Aspergillus niger* | 40 | 36 | 145258936 |
| 4 | *Aspergillus oryzae* RIB40 | 41 | 40 | 169768191 |
| 5 | *Aspergillus fumigatus* Af293 | 41 | 38 | 70986662 |
| 6 | *Neosartorya fischeri* NRRL 181 | 41 | 38 | 119483224 |
| 7 | *Gibberella zeae* PH-1 | 40 | 39 | 46109768 |
| 8 | *Hyphomonas neptunium* ATCC 15444 | 44 | 40 | 114797240 |
| 9 | *Mycobacterium vanbaalenii* PYR-1 | 50 | 91 | 120405468 |
| 10 | *Mesorhizobium loti* MAFF303099 | 38 | 37 | 13471580 |
| 11 | *Mesorhizobium loti* | 35 | 37 | 20804076 |
| 12 | *Roseobacter* sp. MED193 | 37 | 37 | 86137542 |
| 13 | *Marinomonas* sp. MED121 | 36 | 34 | 87122653 |
| 14 | *Rhizobium etli* CIAT 652 | 33 | 32 | 190895112 |
| 15 | *Rhodoferax ferrireducens* T118 | 38 | 36 | 89899273 |
| 16 | *Jannaschia* sp. CCS1 | 37 | 32 | 89053613 |
| 17 | *Labrenzia alexandrii* DFL-11 | 42 | 36 | EEE43073 |
| 18 | *Burkholderia* sp. 383 | 32 | 32 | 78059900 |
| 19 | *Burkholderia cenocepacia* HI2424 | 36 | 33 | ABK12047 |
| 20 | Alpha proteobacterium HTCC2255 | 36 | 34 | ZP_01448442 |
| 21 | Gamma proteobacterium | 27 | 26 | |
| | *Mycobacterium aurum* | 49 | 100 | SEQ ID 5 |
| | *Arthrobacter* sp. | 100 | 49 | SEQ ID 7 |

AS: *Aspergillus* sp., MA: *Mycobacterium aurum*

Example 2

Preparation and Analysis of the Transaminases of *Aspergillus Terreus, Mycobacterium Vanbaalenii* and *Mesorhizobium Loti*

2.1 The ω-TA from *Mycobacterium vanbaalenii*, entry 9 in Table 1 (SEQ ID no. 49 and 50), from *Aspergillus terreus*, entry 1 in table 1 (SEQ ID no. 3 and 4), and *Mesorhizobium loti*, entry 11 in table 1 (SEQ ID no. 1 and 2), have been obtained and used in codon usage adapted form (to *E. coli*) to express the enzymes in *Escherichia coli*. The *Mycobacterium vanbaalenii* transaminase is called in the following Mva-TA, the *Aspergillus terreus* transaminase Ate-TA and the *Mesorhizobium loti* Mlo-TA.

2.2 Acetophenonassay

The Mva-TA and Ate-TA converted (R)-α-MBA at least 100 times faster than the (S)-enantiomer in an acetophenon-assay with 2.5 mM amine and 2.5 mM pyruvate at pH 7.5 and 30° C.

Assay: The increase in absorbtion of the acetophenone formed during the reaction was monitored at 245 nm.

The Mlo-TA did not convert either (R)— nor (S)-α-MBA.

In the following, further amines have been tested in the presence of pyruvate or α-ketoglutarate as amino acceptors (10 mM amine, 10 mM pyruvate, 0.1 mM PLP, phosphate buffer pH 7.5, incubation 24 h at 30° C., analysis by thin layer chromatography).

A conversion could be seen for 2-aminoheptane, 2-aminopentane, 1,3-dimethylbutylamine and 4-phenyl-2-aminobutane. Also, a minimal conversion of isopropylamine could be detected.

No conversion with other amino donors such as D-alanine, L-valine, γ-aminobutyrate, ethylamine, benzyl amine, putrescine, 2-amino-3-methylbutane and 3,3-dimethyl-2-aminobutane could be detected.

Thus, all three proteins were proven to be ω-TA.

In particular, using (R)- and (S)-2-aminohexane as substrate, only the (R)-enantiomer was significantly converted. Thus, also Mlo-TA is a (R)-selective ω-TA. No DATA (D-amino acid transaminase) or BCAT (branched chain aminotransferase) activity was seen for all three proteins.

2.3 Conductivity Assay

Also, 1-N-boc-3-aminopyrrolidine (B3AP), 1-N-boc-3-aminopiperidine (B3APi) and 1-Cbz-3-aminopiperidine (C3APi) were used as substrates to determine the relative activities of these substances against the model substrate α-MBA.

During the reaction of the amine and pyruvate (at pH 7.5 both substrates are charged) to alanine and ketone (the ketone has no charge, alanine is a zwitterionic compound and does not contribute to conductivity) monitoring of the kinetics of the conductivity allows to conclude on the conversion rates.

Before starting the reaction, a calibration was carried out by determining different conversions in dependence of various concentrations of alanine, pyruvate, ketone, and amine.

The reduction in conductivity was per mM conversion of α-MBA, B3AP, B3APi and C3APi 44 μS, 50 μS, 48.5 μS and 49.3 μS.

In addition to the three recombinantly expressed transaminases, a commercially available (R)-selective ATA-117 from Codexis was tested using the following reaction conditions: 50 mM CHES buffer, pH 7.5, pH adjustment with BIS-TRIS (=Bis(2-hydroxyethyl)amino-tris(hydroxymethyl)methane), 0.1 mM PLP, 5-6 mM amine and pyruvate, reaction at 25° C.

A conversion of the substrates could be shown for Ate-TA. The relative activities were 2% for (R)-B3AP and (R,S)-C3APi and 1% for (R)-B3APi compared to (R)-α-MBA.

2.4 Determination of the Enantioselectivity by Asymmetric Synthesis of Amines of Both (R)-Selective ω-TA from *Aspergillus terreus* and *Mesorhizobium loti*

By an independent method it is shown that Mlo and Ate-TA are (R)-selective and convert the substrates to the desired products with excellent enantioselectivity.

For the definitive proof of (R)-enantioselectivity of both transaminases an asymmetric synthesis of different amines were carried out and the optical purity thereof was determined.

As amino donor a hundred-fold excess of alanine was used. The conversion was not exactly determined, but roughly estimated. In further experiments different methods for increasing the conversion (PDC) could be developed. High to excellent enantioselectivities were obtained with both transaminases, except with C3APi, wherein only a very low enantioselectivity was obtained.

TABLE 2

| Amine | Ate-TA % ee | Ate-TA % c | Mlo-TA % ee | Mlo-TA % c |
|---|---|---|---|---|
| B3AP | 99.8 | 40 ± 20 | — | — |
| C3AP | 99.6 | 40 ± 20 | — | — |
| B3APi | >99.9 | 30 ± 20 | — | — |
| C3APi | 49 | 30 ± 20 | | |
| MPPA | — | — | 98 | 15 ± 10 |

Methods:

The transaminases were expressed in *E. coli* BL21.

The culture medium (50 ml LD-Amp medium) was induced with 0.2% of rhamnose, when an optical density (OD) of 0.5 was obtained, and was cultivated for 12 hours at 25° C. Subsequently, the cells were washed with a sodium phosphate buffer, centrifuged, suspended in 1 ml sodium phosphate buffer (pH 7.5) and frozen in 200 μl aliquots.

For the biocatalysis 5 μl of a 500 mM ketone solution in DMSO, 22 mg D-alanine and 10 μl of a 10 mM PLP were added to these aliquots. The reaction mixture was filled up to a total volume of 500 μl with a 50 mM sodium phosphate buffer (pH 7.5). The reaction mixtures were incubated over night at 25° C. and 500 rpm. For determination of the enantiomeric excess by means of CE 200 μl of a 1 N NaOH was added to 400 μl of the sample, extracted with 400 μl of dichloromethane and the organic phase was separated. The organic phase was then extracted with 100 μl of a 5 mM triethylammonium phosphate buffer (pH 3). Subsequently, the obtained aqueous phase was injected in the CE.

The Program of Separation:

CE-Capillare 30 cm, 50 μm inner diameter, temperature 15° C.

- rinsing with triethylammoniumphosphat buffer pH 3, 1 min, 30 psi
- rinsing with 5% highly sulfated cyclo dextrin (HSαCD or HSγCD), 1 min, 10 psi
- injection: 5-10 s, 1 psi
- water dip
- separation: voltage 10 or 15 kV
- detection: MPPA, C3AP and C3APi at 200 nm; B3AP, B3APi at 190 nm Conditions of Separation:

TABLE 3

| | Separating segment [cm] | Chiral selector | Migration time [min] S-Amin | Migration time [min] R-Amin | Voltage while separating |
|---|---|---|---|---|---|
| MPPA | 10 | HSγCD | 2.4 | 2.8 | 15 kV |
| B3AP | 10 | HSγCD | 4.55 | 6.1 | 15 kV |
| B3APi | 20 | HSγCD | 12.0 | 12.4 | 15 kV |
| C3AP | 20 | HSαCD | 10.2 | 11.3 | 10 kV |
| C3APi | 20 | HSαCD | 6.8 | 7.2 | 15 kV |

Example 4

Preparation and Analysis of all Transaminases Identified in Table 1

4.1 Expression and Purification of the Transaminases

The codon optimized open reading frames encoding proteins with entry numbers 1, 2, 3, 4, 8, 9, 11, 13, 14, 15, 17, 18 and 21 in Table 1 were inserted into pGASTON between the NdeI and BamHI restriction sites using a ligation independent cloning strategy. The codon optimized ORF encoding all other proteins were ordered already subcloned into pET-22b. Transformed *E. coli* BL21 (DE3) strains were grown in 400 ml LB medium supplemented with ampicillin (100 μg/ml). Cells were incubated initially at 37° C. on a gyratory shaker until the $OD_{600}$ reached 0.7. The cells were then induced by the addition of 0.2% rhamnose (pGASTON) or 0.1 mM IPTG (pET-22b), respectively, and at the same time the incubation temperature was decreased to 20° C. After induction the incubation was continued for a further 20 h. Aliquots were withdrawn at several points of time after induction to follow the expression.

The cell pellet (~3 g wet weight) was washed twice with phosphate buffer (pH 7.5, 50 mM), containing 0.1 mM PLP at 4° C. After disruption (french press) the cell suspension was centrifuged (4000×g, 30 min) and the resulting supernatant was passed through a 0.5 μm filter prior to chromatography. Chromatography was performed using an ÄKTA Purifier (GE Healthcare). The filtered cellular extract was applied to a 5 ml column of IMAC Sepharose™ 6 Fast Flow (GE Healthcare). The column was washed at a flow rate of 5 ml min-1 with a 10 column-volume of 50 mM phosphate buffer, pH 7.5, containing 300 mM NaCl, 0.1 mM PLP and 30 mM imidazol (to avoid unspecific binding) and the ATA activity was eluted with 10 column-volumes of phosphate buffer (pH 7.5, 50 mM), containing 300 mM NaCl, 0.1 mM PLP and 300 mM imidazol (flow rate of 5 ml min-1). The activity containing fractions were pooled and desalted via gel-chromatography with a 20 mM Tricine-buffer pH 7.5 containing 0.01 mM PLP. The purified enzymes were stored at 4° C.

The amount of each protein purified from approximately 3 g cells (wet weight) is given in Table 4 below.

TABLE 4

| Entry | Enzyme source | Protein yield after purification [mg] |
|---|---|---|
| 1 | *Aspergillus terreus* | 8.6 |
| 2 | *Penicillium chrysogenum* | 26.2 |
| 3 | *Aspergillus niger* | — |
| 4 | *Aspergillus oryzae* | 20.6 |
| 5 | *Aspergillus fumigatus* | 14.8 |
| 6 | *Neosartorya fischeri* | 23.3 |
| 7 | *Gibberella zeae* | 4.8 |
| 8 | *Hyphomonas neptunium* | 6.5 |
| 9 | *Mycobacterium vanbaalenii* | 8.9 |
| 10 | *Mesorhizobium loti* MAFF303099 | 6.9 |
| 11 | *Mesorhizobium loti* | 5.3 |
| 12 | *Roseobacter* sp. | 27.5 |
| 13 | *Marimonas* sp. | 23.7 |
| 14 | *Rhizobium etli* | 6.5 |
| 15 | *Rhodoferax ferrireducens* | 7.5 |
| 16 | *Jannaschia* sp. | 24.8 |
| 17 | *Labrenzia alexandrii* | 12.5 |
| 18 | *Burkholderia* sp. | 41.6 |
| 19 | *Burkholderia cenocepacia* | — |
| 20 | alpha proteobacterium | — |
| 21 | gamma proteobacterium | 2.6 |

4.2 Characterization of Substrate Specificity of (R)-Selective ω-TA

For determining activity towards α-methylbenzyl amine (α-MBA) in the initial screen of the expressed proteins, an acetophenone-based assay was used: a solution of 2.5 mM (R) or (S)-α-MBA and pyruvate was reacted in the presence of the purified enzyme and the increase in absorbance at 245 nm was correlated to the formation of acetophenone. The conversions of the amines 2-aminohexane, 4-phenyl-2-aminobutane and 1-N-Boc-3-aminopyrrolidine were monitored using a conductivity assay: A solution containing 10 mM amine and pyruvate was reacted in the presence of the purified amine transaminase and the decrease in conductivity was related to the conversion of substrate.

For investigating DATA- and BCAT-activity the decrease of NADH was measured spectrophotometrically at 340 nm using dehydrogenase coupled assays: a solution of 5 mM α-ketoglutaric acid and D-alanine was reacted in the presence of the purified transaminase, 1 U/ml lactate dehydrogenase and 0.5 mM NADH for measuring DATA-activity. A solution containing 5 mM 3-methyl-2-oxobutyric acid and L-glutamate, 10 mM ammonium chloride, 1 U/ml glutamate dehydrogenase and 0.5 mM NADH was used for measuring BCAT-activity.

All reactions took place in 20 mM Tricine buffer pH 7.5 containing 0.01 mM PLP. The pH of the buffer was adjusted with 1,8-Diazabicyclo[5.4.0]undec-7-en.

Results are given in Table 5 below.

was performed using CE as described above. The enantiomeric excess (% ee) value for 1 was analysed by GC. After extraction of the amine with ethyl acetate, derivatization to the trifluoroacetamide was performed by adding a 20-fold

TABLE 5

Specific activities for various substrates.

| | Substrates | | | | | | | | | |
|---|---|---|---|---|---|---|---|---|---|---|
| | pyruvate 1 | | pyruvate 2 | | pyruvate 3 | | pyruvate 4 | | 2KG | MOB |
| Entry | R | S | R | S | R | S | R | S | D-Ala | L-Glu |
| 1 | 15.2 | <0.001 | 2.91 | <0.001 | 9.7 | <0.001 | 0.031 | <0.001 | <0.001 | 0.003 |
| 2 | 1.3 | <0.001 | 1.1 | 0.044 | 5.6 | <0.001 | 0.264 | <0.001 | <0.001 | <0.001 |
| 3 | —[a)] | — | — | — | — | — | — | — | — | — |
| 4 | 3.7 | 0.001 | 1.4 | 0.023 | 5.2 | 0.002 | 0.051 | 0.002 | <0.001 | <0.001 |
| 5 | 4.1 | <0.001 | 2.4 | <0.001 | 4.5 | <0.001 | 0.009 | <0.001 | <0.001 | 0.005 |
| 6 | 4.5 | <0.001 | 7.4 | <0.001 | 6.0 | <0.001 | 0.013 | <0.001 | <0.001 | 0.005 |
| 7 | 18.6 | <0.001 | 19.6 | <0.001 | 8.2 | <0.001 | <0.001 | <0.001 | <0.001 | 0.016 |
| 8 | 3.6 | <0.001 | 3.2 | 0.225 | 20.7 | <0.001 | 0.163 | <0.001 | <0.001 | 0.012 |
| 9 | 4.7 | <0.001 | 5.6 | <0.001 | 2.6 | <0.001 | <0.001 | <0.001 | <0.001 | 0.003 |
| 10 | 0.011 | <0.001 | 0.003 | <0.001 | 0.010 | <0.001 | 0.001 | <0.001 | 0.004 | 0.004 |
| 11 | 0.013 | <0.001 | 0.124 | <0.001 | 0.002 | <0.001 | <0.001 | <0.001 | <0.001 | 0.005 |
| 12 | 0.003 | <0.001 | 0.001 | <0.001 | 0.001 | <0.001 | 0.001 | <0.001 | 0.003 | 0.002 |
| 13 | 0.002 | <0.001 | 0.020 | <0.001 | 0.003 | <0.001 | <0.001 | <0.001 | <0.001 | 0.003 |
| 14 | 0.867 | <0.001 | 0.012 | <0.001 | 0.260 | <0.001 | <0.001 | <0.001 | 0.020 | 0.016 |
| 15 | 0.056 | <0.001 | 0.001 | <0.001 | 0.307 | <0.001 | <0.001 | <0.001 | 0.010 | 0.098 |
| 16 | 0.059 | 0.007 | 0.071 | 0.002 | 0.370 | 0.068 | 0.022 | <0.001 | 0.062 | 0.020 |
| 17 | 0.060 | 0.003 | 0.073 | 0.001 | 0.120 | 0.027 | 0.205 | 0.002 | 0.063 | 0.023 |
| 18 | 0.017 | <0.001 | 0.002 | <0.001 | 1.1 | 0.007 | <0.001 | <0.001 | <0.001 | 0.001 |
| 19 | —[a)] | — | — | — | — | — | — | — | — | — |
| 20 | — | — | — | — | — | — | — | — | — | — |
| 21 | 0.028 | <0.001 | 0.610 | 0.004 | 0.034 | <0.001 | <0.001 | <0.001 | <0.001 | 0.031 |

1—aminohexane, 2—α-MBA, 3—4-phenyl-2-aminobutane, 4—1-N-Boc-3-aminopyrrolidine, 2KG—2-ketoglutarate, D-Ala—D-alanine, L-Glu—L-glutamate, MOB—3-methyl-2-oxobutyric acid. Entry number corresponds to Table 1. All measurements were done at least in duplicates. The deviation of single measurements from the mean value was < 10%.

[a)]Measurement was not possible since protein yield during expression was very low/protein was unstable during purification.

4.3 Asymmetric Synthesis of (R)-Amines 1-4 (see Legend of Table 5 Above) with ω-TAs from *Aspergillus terreus, Mesorhizobium loti* and *Mycobacterium vanbaalenii*

Asymmetric syntheses were performed at 30° C. for 24 hours in sodium phosphate buffer (100 mM, pH 7) containing pyridoxal-5'-phosphate PLP monohydrate (1 mM) and NAD+ (1 mM) in 1.5 ml Eppendorf tubes.

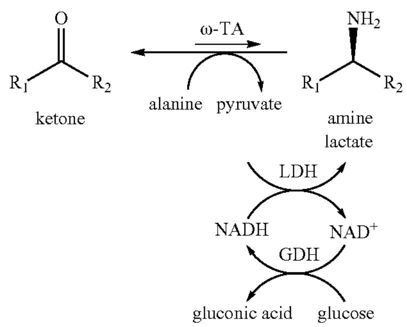

The reaction mixture contained 50 mM ketone, L-alanine (5 equiv., 250 mM), lactate dehydrogenase from bovine heart (90 U), glucose (150 mM) and glucose dehydrogenase (15 U). ω-TA from *Aspergillus terreus, Mesorhizobium loti* and *Mycobacterium vanbaalenii* (entry 1, 11 and 9 in Table 1) were expressed in *E. coli* BL21 as described above, frozen in aliquots and applied directly as whole cell biocatalysts without further purification. The conversion was measured by detection of the formed amines (1, gas chromatography (GC); 2-4, capillary electrophoresis (CE)). Chiral analysis of 2-4 excess of trifluoroacetic acid anhydride. After purging with nitrogen to remove excess anhydride and residual trifluoroacetic acid, the derivatized compound was dissolved in ethyl acetate (50 μl) and baseline separated by using a Shimadzu GC14A that was equipped with a Heptakis-(2,3-di-O-acetyl-6-O-tert-butyldimethylsilyl)-β-cyclodextrin column (25 m×0.25 mm). The retention times were 16.0 min ((S)-1) and 16.2 min ((S)-2) at an oven temperature gradient of 80° C./10 min//20° C.//180° C./10 min.

Results are given in Table 6 below.

TABLE 6

| formed amines | ω-TA | Conversion [%][b] | Enantiomeric excess [% eeP][c] |
|---|---|---|---|
| 1 | Ate | 32 | >99 |
| 1 | Mlo | 41 | >99 |
| 1 | Mva | 35 | >99 |
| 2 | Ate | 15 | >99 |
| 2 | Mlo | 1 | 95.0 |
| 2 | Mva | 2 | >99 |
| 3 | Ate | 14 | >99 |
| 4 | Ate | 11 | >99 |

[a]Reaction conditions: 50 mM ketone, 250 mM D-alanine, 100 mM sodium phosphate buffer pH 7.0, 1 mM PLP, 1 mM NADH. The co-product pyruvate of the reaction was removed with lactate dehydrogenase (LDH). For cofactor recycling, glucose dehydrogenase (GDH) was used.

[b]Conversions were not optimized. The deviation of a single measurement from the mean value did not exceed 10%. Compound 4 was only converted by Ate-TA.

[c](R)-enantiomers.

The invention claimed is:

1. A process for the preparation and screening of a (R)-selective ω-transaminase, comprising the following steps:

a) providing at least one (R)-selective ω-transaminase sequence and at least one biomolecule bank, b) searching the biomolecule bank with the (R)-selective ω-transaminase sequence to identify a group of first target biomolecule sequences, wherein the first target biomolecule sequences have a degree of sequence identity of at least 20% to the query biomolecule sequence, calculated on amino acid level, c) selecting in the group of first target biomolecule sequences a group of second target biomolecule sequences, which do not comprise, on amino acid level, at least one of the following amino acid sequence motives c1) to c3) with c1) at position 95 to 97 an amino acid sequence Tyr Xa1 Xa2, with Xa1 being an amino acid Ile, Val, Leu, Met, Phe, and Xa2 being an amino acid Arg or Lys or c2) at position 97 to 99 an amino acid sequence Tyr Xaa Gln, with Xaa being an amino acid and in the region from position 105 to 111 an amino acid sequence Arg Xaa Xa3, Xa3 being an amino acid, preferably being His or c3) at position 38 Thr, at position 97 Lys and at position 107 to 109 an amino acid sequence Arg Xa4 Xa5, Xa4 being an amino acid, preferably being Gly and Xa5 being an amino acid, preferably being Tyr and which comprise c4) at position 95 an amino acid other than Tyr, Arg, Lys, or at position 95 Tyr, but at position 97 no Arg or Lys and c5) at position 40 no Lys or Arg and c6) in the region from position 161 to 165, a Lys to identify the group of second target biomolecule sequences; and d) providing an isolated biomolecule having or encoding one of the second target biomolecule sequences identified in step c);

e) testing whether the isolated protein biomolecule has an (R)-selective ω-transaminase activity.

2. The process according to claim 1, wherein the biomolecule is a protein and the biomolecule sequence is an amino acid sequence.

3. The process according to claim 1, wherein the biomolecule is a DNA molecule and the biomolecule sequence is a DNA sequence.

4. The process according to claim 1, wherein the biomolecule bank is a biomolecule database and the biomolecule database is searched in step b) with a biomolecule sequence alignment tool, in particular BLAST.

5. The process according to claim 1, wherein the protein or DNA molecule provided in step d) is provided by de novo synthesis.

6. The process according to claim 1, wherein the biomolecule bank is a gene bank and the gene bank is searched in step b) with a query DNA sequence molecule.

7. The process according to claim 6, wherein in step c) DNA-sequence primers are used to select for the group of second bio-molecule sequences.

8. A method of claim 1, wherein step e) comprises the following steps:

i) providing a charged amino acceptor, a charged amino donor and a putative transaminase, ii) reacting the amino acceptor and the amino donor with the transaminase in a reaction medium, and thereby iii) determining the conductivity of the reaction medium under a first set of reaction conditions and iv) subsequently to step iii) determining the conductivity of the reaction medium under a second set of reaction conditions, so as to obtain at least two conductivity values reflecting the properties of the transaminase.

* * * * *

SEQUENCE LISTING

<160> NUMBER OF SEQ ID NOS: 50

<210> SEQ ID NO 1
<211> LENGTH: 322
<212> TYPE: PRT
<213> ORGANISM: Mesorhizobium loti

<400> SEQUENCE: 1

```
Met Thr Leu Ala Thr Thr Asp Ala Thr Val Gly Val Pro Glu Val Glu
1               5                   10                  15

Thr Thr His Lys Asp Thr Arg Arg Tyr Pro His Gly Val Ala Phe Met
            20                  25                  30

Asp Gly Gln Tyr Leu Pro Met Ser Glu Ala Lys Ile Ser Val Leu Asp
        35                  40                  45

Trp Gly Phe Leu His Ser Asp Ala Thr Tyr Asp Thr Val His Val Trp
    50                  55                  60

Glu Gly Arg Phe Phe Arg Leu Asp Leu His Leu Asp Arg Phe Phe Arg
65                  70                  75                  80

Gly Met Asp Arg Leu Arg Met Lys Leu Pro Tyr His Arg Arg Glu Val
                85                  90                  95

Glu Arg Val Leu Ser Asn Cys Val Ala Leu Ser Gly His Lys Ser Ala
            100                 105                 110

Tyr Val Glu Met Ile Cys Thr Arg Gly Gly Ser Pro Thr Phe Ser Arg
        115                 120                 125

Asp Pro Arg Glu Ala Glu Asn Arg Phe Ile Ala Phe Ala Val Pro Phe
    130                 135                 140

Gly Ser Val Ala Asn Lys Glu Gln Leu Glu Arg Gly Leu His Val Gly
145                 150                 155                 160

Val Ser Glu Thr Val Arg Ile Pro Pro Lys Ser Val Asp Pro Thr Ile
                165                 170                 175

Lys Asn Tyr His Trp Leu Asp Leu Val Arg Gly Leu Tyr Asp Ala Tyr
            180                 185                 190

Asp Val Gly Ala Glu Thr Ala Leu Ile Met Asp Thr Asn Gly Asn Ile
        195                 200                 205

Ala Glu Gly Pro Gly Phe Asn Val Phe Thr Val Lys Asn Arg Gln Leu
    210                 215                 220

Lys Thr Pro Ala Phe Gly Val Leu Pro Gly Ile Thr Arg Gln Ser Val
225                 230                 235                 240

Phe Asp Leu Cys Gly Glu Val Gly Leu Ala Val Thr Ala Ala Asp Leu
                245                 250                 255

Pro Arg Leu Glu Leu Gly Glu Ala Asp Glu Val Phe Ile Thr Ser Thr
            260                 265                 270

Ala Gly Gly Ile Met Pro Val Thr Arg Val Asp Gly Ser Ser Ile Gly
        275                 280                 285

Ser Gly Lys Val Gly Val Val Thr Arg Gln Leu Met Asp Leu Tyr Trp
    290                 295                 300

Gln Lys His Ser Asp Asp Ala Trp Ser Thr Pro Val Lys Tyr Ala Ser
305                 310                 315                 320

Gly Ser
```

<210> SEQ ID NO 2
<211> LENGTH: 969
<212> TYPE: DNA
<213> ORGANISM: Mesorhizobium loti

<400> SEQUENCE: 2

```
atgaccctgg caaccaccga tgcaaccgtt ggtgttccgg aagttgaaac cacccataaa     60
gatacccgtc gttatccgca tggtgttgca tttatggatg gtcagtatct gccgatgagc    120
gaagcaaaaa ttagcgttct ggattggggt tttctgcatt ctgatgccac ctatgatacc    180
gttcatgttt gggaaggtcg ttttttttcgt ctggatctgc atctggatcg ctttttttcgt   240
ggtatggatc gtctgcgtat gaaactgccg tatcatcgtc gtgaagttga acgtgttctg    300
agcaattgtg ttgcactgag cggtcataaa agcgcctatg tggaaatgat ttgtacccgt    360
ggtggtagcc cgacctttag ccgtgatccg cgtgaagcag aaaatcgctt tattgcattt    420
gcagttccgt ttggttctgt ggcaaataaa gaacagctgg aacgtggtct gcatgttggt    480
gttagcgaaa ccgttcgtat tcctccgaaa agcgttgatc cgaccattaa aaattatcat    540
tggctggatc tggttcgtgg tctgtatgat gcctatgatg ttggtgcaga aaccgcactg    600
attatggata ccaatggcaa tattgcagaa ggtccgggtt ttaacgtgtt taccgtgaaa    660
aatcgtcagc tgaaaacacc ggcatttggt gttctgcctg gtattacacg tcagagcgtt    720
tttgatctgt gtggtgaagt tggtctggca gttaccgcag cagatctgcc tcgtctggaa    780
ctgggtgaag cagatgaagt ttttattacc agcaccgcag gcggcattat gccggttacc    840
cgtgttgatg gtagcagcat tggtagcggt aaagttggtg ttgttacccg tcagctgatg    900
gatctgtatt ggcagaaaca ttctgatgat gcatggtcta caccggttaa atatgcctca    960
ggatcctga                                                            969
```

<210> SEQ ID NO 3
<211> LENGTH: 328
<212> TYPE: PRT
<213> ORGANISM: Aspergillus terreus

<400> SEQUENCE: 3

```
Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80

Glu Ala Ser Cys Thr Lys Leu Arg Leu Arg Leu Pro Leu Pro Arg Asp
                85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125

Gly Thr Arg Pro Glu Asp Ile Val Asn Asn Leu Tyr Met Phe Val Gln
    130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
            180                 185                 190
```

```
Glu Ala Ala Asp Arg Gly Ala Thr Tyr Pro Phe Leu Thr Asp Gly Asp
        195                 200                 205

Ala His Leu Thr Glu Gly Ser Gly Phe Asn Ile Val Leu Val Lys Asp
    210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255

Glu Phe Val Pro Val Glu Leu Ala Tyr Arg Cys Asp Glu Ile Phe Met
            260                 265                 270

Cys Thr Thr Ala Gly Gly Ile Met Pro Ile Thr Thr Leu Asp Gly Met
        275                 280                 285

Pro Val Asn Gly Gly Gln Ile Gly Pro Ile Thr Lys Lys Ile Trp Asp
    290                 295                 300

Gly Tyr Trp Ala Met His Tyr Asp Ala Ala Tyr Ser Phe Glu Ile Asp
305                 310                 315                 320

Tyr Asn Glu Arg Asn Ser Gly Ser
                325


<210> SEQ ID NO 4
<211> LENGTH: 987
<212> TYPE: DNA
<213> ORGANISM: Aspergillus terreus

<400> SEQUENCE: 4

atggcaagca tggataaagt ttttgccggt tatgcagcac gtcaggcaat tctggaaagc      60

accgaaacca ccaatccgtt tgcaaaaggt attgcatggg ttgaaggtga actggttccg     120

ctggcagaag cacgtattcc gctgctggat cagggtttta tgcatagcga tctgacctat     180

gatgttccga gcgtttggga tggtcgtttt tttcgtctgg atgatcatat tacccgtctg     240

gaagccagct gtaccaaact gcgtctgcgt ctgccgctgc ctcgtgatca ggttaaacaa     300

attctggttg aaatggttgc caaaagcggt attcgtgatg catttgtgga actgattgtt     360

acccgtggtc tgaaaggtgt tcgtggcacc cgtccggaag atatcgtgaa taatctgtat     420

atgtttgtgc agccgtatgt ttgggttatg gaaccggata tgcagcgtgt tggtggtagc     480

gcagttgttg cacgtaccgt tcgtcgtgtt ccgcctggtg caattgatcc gaccgttaaa     540

aatctgcagt ggggtgatct ggttcgtggt atgtttgaag cagcagatcg tggtgcaacc     600

tatccgtttc tgaccgatgg tgatgcacat ctgaccgaag gtagcggttt taacattgtg     660

ctggtgaaag atggtgttct gtatacaccg gatcgtggtg ttctgcaggg tgttacacgt     720

aaaagcgtga ttaatgcagc agaagccttt ggtattgaag tgcgtgttga atttgttccg     780

gttgaactgg catatcgctg tgatgaaatt tttatgtgta ccaccgcagg cggtattatg     840

ccgattacca ccctggatgg tatgccggtt aatggtggtc agattggtcc gattaccaaa     900

aaaatttggg atggctattg ggcaatgcat tatgatgcag cctatagctt tgaaattgat     960

tataatgaac gcaattcagg atcctga                                         987


<210> SEQ ID NO 5
<211> LENGTH: 339
<212> TYPE: PRT
<213> ORGANISM: Mycobacterium aurum

<400> SEQUENCE: 5

Met Thr Ala Leu Ser Asp Leu Gly Thr Ser Asn Leu Val Ala Val Glu
1               5                   10                  15
```

-continued

```
Pro Gly Ala Ile Arg Glu Asp Thr Pro Ala Gly Ser Val Ile Gln Tyr
            20                  25                  30

Ser Asp Tyr Glu Leu Asp Thr Ser Ser Pro Phe Ala Gly Gly Val Ala
        35                  40                  45

Trp Ile Glu Gly Glu Tyr Leu Pro Ala Glu Glu Ala Lys Ile Ser Ile
    50                  55                  60

Phe Asp Thr Gly Phe Gly His Ser Asp Leu Thr Tyr Thr Val Ala His
65                  70                  75                  80

Val Trp His Gly Asn Ile Phe Arg Leu Gly Asp His Leu Asp Arg Leu
                85                  90                  95

Leu Asp Gly Ala Ser Lys Leu Arg Leu Asp Ala Gly Tyr Ser Lys Asp
            100                 105                 110

Glu Leu Ala Glu Ile Thr Lys Lys Cys Val Ser Met Ser Gln Leu Arg
        115                 120                 125

Glu Ser Phe Val Asn Leu Thr Val Thr Arg Gly Tyr Gly Lys Arg Lys
    130                 135                 140

Gly Glu Lys Asp Leu Ser Lys Leu Thr His Gln Val Tyr Ile Tyr Ala
145                 150                 155                 160

Ile Pro Tyr Leu Trp Ala Phe Pro Pro Ala Glu Gln Ile Phe Gly Thr
                165                 170                 175

Thr Ala Ile Val Pro Arg His Val Arg Arg Ala Gly Arg Asn Thr Val
            180                 185                 190

Asp Pro Thr Ile Lys Asn Tyr Gln Trp Gly Asp Leu Thr Ala Ala Ser
        195                 200                 205

Phe Glu Ala Lys Asp Arg Gly Ala Arg Thr Ala Ile Leu Leu Asp Ser
    210                 215                 220

Asp Asn Cys Val Ala Glu Gly Pro Gly Phe Asn Val Cys Ile Val Lys
225                 230                 235                 240

Asp Gly Lys Leu Ala Ser Pro Ser Arg Asn Ala Leu Pro Gly Ile Thr
                245                 250                 255

Arg Lys Thr Val Phe Glu Leu Ala Asp Gln Met Gly Ile Glu Ala Thr
            260                 265                 270

Leu Arg Asp Val Thr Ser Arg Glu Leu Tyr Asp Ala Asp Glu Leu Met
        275                 280                 285

Ala Val Thr Thr Ala Gly Gly Val Thr Pro Ile Asn Ser Leu Asp Gly
    290                 295                 300

Glu Ala Val Gly Asn Gly Glu Pro Gly Pro Leu Thr Val Ala Ile Arg
305                 310                 315                 320

Asp Arg Phe Trp Ala Leu Met Asp Glu Pro Gly Pro Leu Ile Glu Thr
                325                 330                 335

Ile Glu Tyr


<210> SEQ ID NO 6
<211> LENGTH: 1020
<212> TYPE: DNA
<213> ORGANISM: Mycobacterium aurum

<400> SEQUENCE: 6

atgactgctc tttcagacct cggcacctcc aacctggtgg ccgtcgagcc cggcgccatc      60

cgcgaggaca ccccggccgg ctcggtgatc cagtacagcg actacgaact ggacacctcc     120

agcccgttcg ccggcggcgt cgcctggatc gagggcgaat acctgccggc cgaagaagcg     180

aagatctcca tcttcgacac cggattcggt cattccgatc tgacctacac cgtcgcgcat     240

gtatggcacg gcaacatctt ccggctcggc gaccacctgg accggttgct cgacggggcg     300
```

```
tccaagctgc gcctggacgc cgggtacagc aaggacgaac tggccgagat caccaagaag    360

tgcgtgtcga tgtcgcagct gcgcgaatcg ttcgtgaatc tgaccgtcac ccggggatac    420

ggaaagcgca agggcgagaa ggacctgtcc aagctcaccc atcaggtgta catctacgcc    480

atcccgtacc tgtgggcctt cccgcccgcc gagcagatct tcggcaccac cgcgatcgtg    540

ccgcgccatg tccgccgcgc cggccgcaac accgtcgacc cgaccatcaa gaactaccag    600

tggggtgatc tcaccgcagc cagtttcgaa gccaaggacc gtggtgcgcg caccgcgatc    660

ctgctcgact cggacaactg cgtggccgaa ggtccgggct tcaacgtgtg catcgtcaag    720

gacggcaagc tggcctcccc gtcccggaac gcgttgccgg gcatcacccg taagacggtg    780

ttcgaactgg ccgaccagat gggcatcgaa gccaccctgc gcgacgtcac cagccgtgaa    840

ctctacgacg ccgacgagtt gatggcggtc accaccgcgg gcggggtcac accgatcaac    900

tcgctggatg gcgaggccgt gggcaacggc gagcccggtc cactgacggt ggccatccgg    960

gaccggttct gggcgctgat ggacgagccg ggcccgctga tcgaaacgat cgaatactga   1020
```

```
<210> SEQ ID NO 7
<211> LENGTH: 330
<212> TYPE: PRT
<213> ORGANISM: Arthrobacter

<400> SEQUENCE: 7

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Phe Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Ser Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255
```

```
Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
    290                 295                 300

Pro Ile Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 8
<211> LENGTH: 993
<212> TYPE: DNA
<213> ORGANISM: Arthrobacter sp.

<400> SEQUENCE: 8

atggcattca gcgccgatac ctccgagatc gtctacacgc acgacaccgg cctcgactac      60

atcacttata gcgactacga actcgatcct gctaacccgc tcgcgggagg tgcggcatgg     120

atcgagggtg cattcgtgcc gccgtcggag gcgcggatct cgatcttcga tcagggttac     180

ctccactcgg acgtcaccta cacggtcttc cacgtctgga acggaaatgc attccgcctc     240

gacgaccaca tcgaacgcct cttctccaac gcggagtcga tgcgcatcat ccctccgctc     300

acacaggacg aagtgaagga gattgcgctc gaactcgtcg cgaagaccga attgcgtgag     360

gccttcgtgt ccgtgtcgat tacccgcggt tacagctcga ctccgggcga gcgcgacatc     420

acgaagcacc gcccgcaggt gtacatgtat gccgtcccat atcagtggat cgtgccgttt     480

gaccgaattc gcgacggcgt gcacgccatg gtcgcacaga gcgtgcgccg aaccccgcgc     540

agctcgatcg accctcaggt caagaacttc cagtgggggg atctgatccg tgcggttcaa     600

gagacgcacg accgcgggtt cgaggctccc cttctgctcg acggcgatgg actgcttgcc     660

gagggctcgg ggttcaacgt cgtcgtgatc aaggacggcg tcgtgcgcag cccgggtcga     720

gcggcgctcc ccggcattac gcggaagacc gtgctcgaga tcgccgaatc gctcggacac     780

gaggcgattc tcgccgacat cacgctcgct gaactgctcg acgccgacga agtgctcggc     840

tgcacgactg cgggcggagt gtggccattc gtcagcgtgg acggcaaccc catctcggac     900

ggggttcccg gccccatcac ccagtcgatc atccgtcgtt actgggagct gaatgtcgag     960

agctcgtcgt tgcttacgcc tgtgcagtac tga                                  993


<210> SEQ ID NO 9
<211> LENGTH: 9
<212> TYPE: PRT
<213> ORGANISM: Escherichia coli

<400> SEQUENCE: 9

Thr Ser Ala Tyr Ile Arg Pro Leu Ile
1               5


<210> SEQ ID NO 10
<211> LENGTH: 8
<212> TYPE: PRT
<213> ORGANISM: Escherichia coli

<400> SEQUENCE: 10

Val Phe Glu Gly Ile Arg Cys Tyr
1               5
```

<210> SEQ ID NO 11
<211> LENGTH: 8
<212> TYPE: PRT
<213> ORGANISM: Escherichia coli

<400> SEQUENCE: 11

Asp Val Gly Met Gly Val Asn Pro
1 5

<210> SEQ ID NO 12
<211> LENGTH: 9
<212> TYPE: PRT
<213> ORGANISM: Escherichia coli

<400> SEQUENCE: 12

Pro Thr Ala Ala Lys Ala Gly Gly Asn
1 5

<210> SEQ ID NO 13
<211> LENGTH: 960
<212> TYPE: DNA
<213> ORGANISM: Penicillium chrysogenum

<400> SEQUENCE: 13
atggctacaa tggaaaaaat cttcgccgcc taccacgagc gccaaaagct tcttgcagcg 60
aacacccacc ccttcgcaaa aggtgtcgct tgggtggagg gagaacttac tcctctccat 120
gaagcccgta tcccaatcct agaccaaggc ttcatgcaca gcgacttgac atacgatgtt 180
ccctctgtct gggatggacg ctttttccgg ctcgatgacc acatcacccg gttggaagcc 240
agctgcacca agctacgcat gaaactcccc ctcccacgcg acgaggtgaa gcagattctg 300
gtcgatatgg ttgcaaagag tggcatccgc gacgcgtttg tcgaaatcat cgtgacgcgt 360
ggattgaaag gtgtgcgagg ctctcgccct gaggatatcg tcaaccgtat ctatatgttt 420
attcaaccct acgtctggtg tatggaacct gaggtgcagc ctgtgggtgg aagcgcaatt 480
atcgcaagga ctgtccgccg cgtcccgcct ggctgcatcg accccactgt caagaatctg 540
caatggggtg atctggttcg cggccttttc gaggcttctg atcgtggcgc cgaatatccc 600
ttcctgaccg atggtgacac caacctcacc gaaggttccg gcttcaacat tgttctcgtg 660
aaggacaata ttctgtacac tccagctcgc ggagtacttg aaggtgtgac acgcaagagt 720
gtgattgatg tcgctcgagc cagcggcttt gacattaagg tcgagttggt acctgtccaa 780
atggcttatg atgcggatga aatttttatg tgtaccactg ctggaggtat catgcccatc 840
accagtcttg atggcaagcc cgtgaacgac ggaaaggttg ggtctgttac caagaagatc 900
tgggatgggt actgggctat ccactatgat cctgcctaca gcttcgagat tgcctattag 960

<210> SEQ ID NO 14
<211> LENGTH: 319
<212> TYPE: PRT
<213> ORGANISM: Penicillium chrysogenum

<400> SEQUENCE: 14

Met Ala Thr Met Glu Lys Ile Phe Ala Ala Tyr His Glu Arg Gln Lys
1 5 10 15

Leu Leu Ala Ala Asn Thr His Pro Phe Ala Lys Gly Val Ala Trp Val
20 25 30

Glu Gly Glu Leu Thr Pro Leu His Glu Ala Arg Ile Pro Ile Leu Asp
35 40 45

Gln Gly Phe Met His Ser Asp Leu Thr Tyr Asp Val Pro Ser Val Trp
50 55 60

```
Asp Gly Arg Phe Phe Arg Leu Asp Asp His Ile Thr Arg Leu Glu Ala
65                  70                  75                  80

Ser Cys Thr Lys Leu Arg Met Lys Leu Pro Leu Pro Arg Asp Glu Val
                85                  90                  95

Lys Gln Ile Leu Val Asp Met Val Ala Lys Ser Gly Ile Arg Asp Ala
            100                 105                 110

Phe Val Glu Ile Ile Val Thr Arg Gly Leu Lys Gly Val Arg Gly Ser
        115                 120                 125

Arg Pro Glu Asp Ile Val Asn Arg Ile Tyr Met Phe Ile Gln Pro Tyr
    130                 135                 140

Val Trp Cys Met Glu Pro Glu Val Gln Pro Val Gly Gly Ser Ala Ile
145                 150                 155                 160

Ile Ala Arg Thr Val Arg Arg Val Pro Pro Gly Cys Ile Asp Pro Thr
                165                 170                 175

Val Lys Asn Leu Gln Trp Gly Asp Leu Val Arg Gly Leu Phe Glu Ala
            180                 185                 190

Ser Asp Arg Gly Ala Glu Tyr Pro Phe Leu Thr Asp Gly Asp Thr Asn
        195                 200                 205

Leu Thr Glu Gly Ser Gly Phe Asn Ile Val Leu Val Lys Asp Asn Ile
    210                 215                 220

Leu Tyr Thr Pro Ala Arg Gly Val Leu Glu Gly Val Thr Arg Lys Ser
225                 230                 235                 240

Val Ile Asp Val Ala Arg Ala Ser Gly Phe Asp Ile Lys Val Glu Leu
                245                 250                 255

Val Pro Val Gln Met Ala Tyr Asp Ala Asp Glu Ile Phe Met Cys Thr
            260                 265                 270

Thr Ala Gly Gly Ile Met Pro Ile Thr Ser Leu Asp Gly Lys Pro Val
        275                 280                 285

Asn Asp Gly Lys Val Gly Ser Val Thr Lys Lys Ile Trp Asp Gly Tyr
    290                 295                 300

Trp Ala Ile His Tyr Asp Pro Ala Tyr Ser Phe Glu Ile Ala Tyr
305                 310                 315

<210> SEQ ID NO 15
<211> LENGTH: 984
<212> TYPE: DNA
<213> ORGANISM: Aspergillus niger

<400> SEQUENCE: 15

atggcatcca tgaaccaagt tcttactgaa tatgccactc gccgcgcgac actagaagcc      60

agtaaaaacc cctacgccaa gggaatcgcc tgggttgaag ggcaactcgt ccccctcagg     120

gaggcccgca tccccctaat tgatcaaggc tttttacgca gtgatttaac ctacgatgtc     180

atctccgtct gggatggctg gttctttcgc ctagatgacc acctttcccg acttgaattg     240

gcctgcgcga aatcgcgtct caagttgccc atttcccgcg atgaagtgaa acaatccctg     300

gttaggatgg tcgctcaaag tggtattcga gatgcatatg tggctttgat tgtgacgcgg     360

ggattgcaga gtgttcgcgg tgccaagccg gaggacttgg tgaacaacct gtacatgttt     420

gtacaaccct atgtatgggt aatggaacca gaggtccaac gggtcggtgg aagtgctgtt     480

gttactcgaa ctgttcgtcg ggtgccccca ggagctattt atcctactgt aaagaaccta     540

caatggggtg acctgacccg aggtatgctc gaggccgccg atcgaggctc catgtacccg     600

ttcctgacgg atggagatgg ccatctcacc gaggggtccg gatacaatat cgttctaatc     660

aaggccggtg ccatttatac gcctgatcgc ggcgtgctgc atggtgtcac caggacaagt     720
```

```
gtcattgatg ttgcacgagc ttgtggtatc caagttcatc tcgaagctgt gccggtggag    780

ttggtatatc agtgtgatga gatattcatg tgcacaacag caggtggaat catgcccatc    840

actgagctgg atggcaagcc tgtaaatggg gggcggattg gtccgatcac gaagaagatc    900

tgggacgggt attggggtat gcattatgat ccagcctaca gcttcgcagt tagttatgat    960

gacggatcaa aagcaaagct ctga                                            984


<210> SEQ ID NO 16
<211> LENGTH: 327
<212> TYPE: PRT
<213> ORGANISM: Aspergillus niger

<400> SEQUENCE: 16

Met Ala Ser Met Asn Gln Val Leu Thr Glu Tyr Ala Thr Arg Arg Ala
1               5                   10                  15

Thr Leu Glu Ala Ser Lys Asn Pro Tyr Ala Lys Gly Ile Ala Trp Val
            20                  25                  30

Glu Gly Gln Leu Val Pro Leu Arg Glu Ala Arg Ile Pro Leu Ile Asp
        35                  40                  45

Gln Gly Phe Leu Arg Ser Asp Leu Thr Tyr Asp Val Ile Ser Val Trp
    50                  55                  60

Asp Gly Trp Phe Phe Arg Leu Asp Asp His Leu Ser Arg Leu Glu Leu
65                  70                  75                  80

Ala Cys Ala Lys Ser Arg Leu Lys Leu Pro Ile Ser Arg Asp Glu Val
                85                  90                  95

Lys Gln Ser Leu Val Arg Met Val Ala Gln Ser Gly Ile Arg Asp Ala
            100                 105                 110

Tyr Val Ala Leu Ile Val Thr Arg Gly Leu Gln Ser Val Arg Gly Ala
        115                 120                 125

Lys Pro Glu Asp Leu Val Asn Asn Leu Tyr Met Phe Val Gln Pro Tyr
    130                 135                 140

Val Trp Val Met Glu Pro Glu Val Gln Arg Val Gly Gly Ser Ala Val
145                 150                 155                 160

Val Thr Arg Thr Val Arg Arg Val Pro Pro Gly Ala Ile Tyr Pro Thr
                165                 170                 175

Val Lys Asn Leu Gln Trp Gly Asp Leu Thr Arg Gly Met Leu Glu Ala
            180                 185                 190

Ala Asp Arg Gly Ser Met Tyr Pro Phe Leu Thr Asp Gly Asp Gly His
        195                 200                 205

Leu Thr Glu Gly Ser Gly Tyr Asn Ile Val Leu Ile Lys Ala Gly Ala
    210                 215                 220

Ile Tyr Thr Pro Asp Arg Gly Val Leu His Gly Val Thr Arg Thr Ser
225                 230                 235                 240

Val Ile Asp Val Ala Arg Ala Cys Gly Ile Gln Val His Leu Glu Ala
                245                 250                 255

Val Pro Val Glu Leu Val Tyr Gln Cys Asp Glu Ile Phe Met Cys Thr
            260                 265                 270

Thr Ala Gly Gly Ile Met Pro Ile Thr Glu Leu Asp Gly Lys Pro Val
        275                 280                 285

Asn Gly Gly Arg Ile Gly Pro Ile Thr Lys Lys Ile Trp Asp Gly Tyr
    290                 295                 300

Trp Gly Met His Tyr Asp Pro Ala Tyr Ser Phe Ala Val Ser Tyr Asp
305                 310                 315                 320

Asp Gly Ser Lys Ala Lys Leu
```

325

<210> SEQ ID NO 17
<211> LENGTH: 981
<212> TYPE: DNA
<213> ORGANISM: Aspergillus oryzae

<400> SEQUENCE: 17

```
atgacatcta tgaacaaagt attttccggt tactacgagc gcaaggctcg tctagataac     60

agtgacaacc gctttgcgaa aggaattgcc tacgtccagg gatctttcgt cccactcgcc    120

gacgcacgag tcccactcct cgacgagggt ttcatgcata gcgacctcac gtacgatgtg    180

ccatcggtct gggatgggcg ctttttccgc cttgatgatc atctcagtcg attggaagat    240

agttgtgaaa agatgcgact gaagatccca ctgtccaggg acgaagtcaa gcaaacccta    300

agggagatgg ttgctaagag tggaatcgaa gatgcctttg tggagctgat cgtcactcgt    360

ggcctgaaag ggtccgtgg caataagcca gaggatcttt tcgacaatca tctctatctg    420

atcgtcatgc cgtatgtctg ggtgatggag cccgccatcc aacataccgg aggtactgcg    480

atcattgccc gtacagtacg gcgcactccc cccggtgctt tcgatcctac catcaagaat    540

ctccagtggg gggacttgac acggggtcta tttgaagcgg ctgaccgtgg cgcggattac    600

ccatttctct cagatggaga taccaatctc acagaaggat ccggtttcaa tatagtgttg    660

gttaaagatg gtattatcta cacgcccgac cgtggtgttc tggaaggcat tacacgtaag    720

agtgtttttg atattgccca ggtcaagaac atcgaggtcc gcgttcaggt ggtgccactc    780

gaacatgcct atcacgccga tgagatattc atgtgtacta ctgctggtgg cattatgcct    840

atcacgaaac tcgatgggaa accgatccgg aatggagaag tcggtcccct tactacaaag    900

atatgggatg agtactgggc gatgcactat gacccgaaat atagctctgc tatcgattac    960

aggggccatg agggtaactg a                                              981
```

<210> SEQ ID NO 18
<211> LENGTH: 326
<212> TYPE: PRT
<213> ORGANISM: Aspergillus oryzae

<400> SEQUENCE: 18

```
Met Thr Ser Met Asn Lys Val Phe Ser Gly Tyr Tyr Glu Arg Lys Ala
1               5                   10                  15

Arg Leu Asp Asn Ser Asp Asn Arg Phe Ala Lys Gly Ile Ala Tyr Val
            20                  25                  30

Gln Gly Ser Phe Val Pro Leu Ala Asp Ala Arg Val Pro Leu Leu Asp
        35                  40                  45

Glu Gly Phe Met His Ser Asp Leu Thr Tyr Asp Val Pro Ser Val Trp
    50                  55                  60

Asp Gly Arg Phe Phe Arg Leu Asp Asp His Leu Ser Arg Leu Glu Asp
65                  70                  75                  80

Ser Cys Glu Lys Met Arg Leu Lys Ile Pro Leu Ser Arg Asp Glu Val
                85                  90                  95

Lys Gln Thr Leu Arg Glu Met Val Ala Lys Ser Gly Ile Glu Asp Ala
            100                 105                 110

Phe Val Glu Leu Ile Val Thr Arg Gly Leu Lys Gly Val Arg Gly Asn
        115                 120                 125

Lys Pro Glu Asp Leu Phe Asp Asn His Leu Tyr Leu Ile Val Met Pro
    130                 135                 140

Tyr Val Trp Val Met Glu Pro Ala Ile Gln His Thr Gly Gly Thr Ala
```

```
145                 150                 155                 160

Ile Ile Ala Arg Thr Val Arg Arg Thr Pro Pro Gly Ala Phe Asp Pro
                165                 170                 175

Thr Ile Lys Asn Leu Gln Trp Gly Asp Leu Thr Arg Gly Leu Phe Glu
            180                 185                 190

Ala Ala Asp Arg Gly Ala Asp Tyr Pro Phe Leu Ser Asp Gly Asp Thr
        195                 200                 205

Asn Leu Thr Glu Gly Ser Gly Phe Asn Ile Val Leu Val Lys Asp Gly
    210                 215                 220

Ile Ile Tyr Thr Pro Asp Arg Gly Val Leu Glu Gly Ile Thr Arg Lys
225                 230                 235                 240

Ser Val Phe Asp Ile Ala Gln Val Lys Asn Ile Glu Val Arg Val Gln
                245                 250                 255

Val Val Pro Leu Glu His Ala Tyr His Ala Asp Glu Ile Phe Met Cys
            260                 265                 270

Thr Thr Ala Gly Gly Ile Met Pro Ile Thr Lys Leu Asp Gly Lys Pro
        275                 280                 285

Ile Arg Asn Gly Glu Val Gly Pro Leu Thr Thr Lys Ile Trp Asp Glu
    290                 295                 300

Tyr Trp Ala Met His Tyr Asp Pro Lys Tyr Ser Ser Ala Ile Asp Tyr
305                 310                 315                 320

Arg Gly His Glu Gly Asn
                325


<210> SEQ ID NO 19
<211> LENGTH: 972
<212> TYPE: DNA
<213> ORGANISM: Aspergillus fumigatus

<400> SEQUENCE: 19

atggcctcta tggacaaagt cttttcggga tattatgcgc gccagaagct gcttgaacgg     60

agcgacaatc ctttctctaa gggcattgct tatgtggaag gaaagctcgt cttacctagt    120

gatgctagaa taccgctact cgacgaaggt ttcatgcaca gtgacctaac ctatgatgtt    180

atatcggttt gggatggtcg cttctttcga ttggacgatc atttgcaacg gattttggaa    240

agctgcgata agatgcggct caagttccca cttgcactga gctcagtgaa aaatattctg    300

gctgagatgg tcgccaagag tggtatccgg gatgcgtttg tggaagttat tgtgacacgt    360

ggtctgacag gtgtacgtgg ttcgaagcct gaggatctgt ataataacaa catatacctg    420

cttgttcttc catacatttg ggttatggcg cctgagaacc agctccatgg tggcgaggct    480

atcattacaa ggacagtgcg acgaacaccc ccaggtgcat ttgatcctac tatcaaaaat    540

ctacagtggg gtgatttaac aaagggactt tttgaggcaa tggaccgtgg cgccacatac    600

ccatttctca ctgatggaga caccaacctt actgaaggat ctggtttcaa cattgttttg    660

gtgaagaacg gtattatcta taccctgat cgaggtgtct tgcgagggat cacacgtaaa     720

agtgtgattg acgttgcccg agccaacagc atcgacatcc gccttgaggt cgtaccagtg    780

gagcaggctt atcactctga tgagatcttc atgtgcacaa ctgccggcgg cattatgcct    840

ataacattgc ttgatggtca acctgttaat gacggccagg ttggcccaat cacaaagaag    900

atatgggatg gctattggga gatgcactac aatccggcgt atagttttcc tgttgactat    960

ggcagtggct aa                                                        972


<210> SEQ ID NO 20
<211> LENGTH: 323
```

<212> TYPE: PRT
<213> ORGANISM: Aspergillus fumigatus

<400> SEQUENCE: 20

```
Met Ala Ser Met Asp Lys Val Phe Ser Gly Tyr Tyr Ala Arg Gln Lys
1               5                   10                  15

Leu Leu Glu Arg Ser Asp Asn Pro Phe Ser Lys Gly Ile Ala Tyr Val
            20                  25                  30

Glu Gly Lys Leu Val Leu Pro Ser Asp Ala Arg Ile Pro Leu Leu Asp
        35                  40                  45

Glu Gly Phe Met His Ser Asp Leu Thr Tyr Asp Val Ile Ser Val Trp
    50                  55                  60

Asp Gly Arg Phe Phe Arg Leu Asp Asp His Leu Gln Arg Ile Leu Glu
65                  70                  75                  80

Ser Cys Asp Lys Met Arg Leu Lys Phe Pro Leu Ala Leu Ser Ser Val
                85                  90                  95

Lys Asn Ile Leu Ala Glu Met Val Ala Lys Ser Gly Ile Arg Asp Ala
            100                 105                 110

Phe Val Glu Val Ile Val Thr Arg Gly Leu Thr Gly Val Arg Gly Ser
        115                 120                 125

Lys Pro Glu Asp Leu Tyr Asn Asn Asn Ile Tyr Leu Leu Val Leu Pro
    130                 135                 140

Tyr Ile Trp Val Met Ala Pro Glu Asn Gln Leu His Gly Gly Glu Ala
145                 150                 155                 160

Ile Ile Thr Arg Thr Val Arg Arg Thr Pro Pro Gly Ala Phe Asp Pro
                165                 170                 175

Thr Ile Lys Asn Leu Gln Trp Gly Asp Leu Thr Lys Gly Leu Phe Glu
            180                 185                 190

Ala Met Asp Arg Gly Ala Thr Tyr Pro Phe Leu Thr Asp Gly Asp Thr
        195                 200                 205

Asn Leu Thr Glu Gly Ser Gly Phe Asn Ile Val Leu Val Lys Asn Gly
    210                 215                 220

Ile Ile Tyr Thr Pro Asp Arg Gly Val Leu Arg Gly Ile Thr Arg Lys
225                 230                 235                 240

Ser Val Ile Asp Val Ala Arg Ala Asn Ser Ile Asp Ile Arg Leu Glu
                245                 250                 255

Val Val Pro Val Glu Gln Ala Tyr His Ser Asp Glu Ile Phe Met Cys
            260                 265                 270

Thr Thr Ala Gly Gly Ile Met Pro Ile Thr Leu Leu Asp Gly Gln Pro
        275                 280                 285

Val Asn Asp Gly Gln Val Gly Pro Ile Thr Lys Lys Ile Trp Asp Gly
    290                 295                 300

Tyr Trp Glu Met His Tyr Asn Pro Ala Tyr Ser Phe Pro Val Asp Tyr
305                 310                 315                 320

Gly Ser Gly
```

<210> SEQ ID NO 21
<211> LENGTH: 972
<212> TYPE: DNA
<213> ORGANISM: Neosartorya fischeri

<400> SEQUENCE: 21

```
atggcctcta tggacaaagt cttttcggga tatcatgcgc gccagaagct gcttgaacgg     60

agcgacaatc ctttctctaa gggcattgcc tatgtggaag gaaagctcgt cttacccagc    120

gacgccagaa taccgctact tgacgaaggc ttcatgcacg gtgacctaac ttatgatgtt    180
```

```
acaacggttt gggatggacg cttctttcga ttggatgatc atatgcaacg gatcctggaa    240

agctgcgata aaatgcggct caagttccca cttgcaccga gcacggtgaa aaatatcctg    300

gctgagatgg tcgccaagag tggtattcgg gatgcgtttg tggaagttat cgtgacacgt    360

ggtctgacag gtgtacgtgg ttcgaagccc gaggatctgt ataataacaa catatacctg    420

cttgttctcc catacgtttg ggttatggcg cctgagaacc agctccttgg tggcagtgct    480

atcattacaa ggacagtgcg acgaacaccc ccgggtgcat ttgatcctac gatcaaaaat    540

ctacagtggg gtgacttaac aaagggactt tttgaggcaa tggaccgtgg cgcaacgtac    600

ccatttctca ctgacggaga caccaacctt accgaaggat ctggatttaa cattgtcttg    660

gtgaagaacg gtattatcta tacccctgat cgaggtgtct tgcgagggat cacacgtaaa    720

agtgtgattg acgttgcccg agccaacaac atcgacatcc gccttgaggt cgtaccagtg    780

gagcaggttt atcactccga tgaaatcttc atgtgcacaa cagccggtgg cattatgcct    840

ataacgttgc ttgatggtca accagttaat gacggccagg ttggcccgat cacaaagaag    900

atatgggatg gttactggga gatgcactac aatccggcgt atagttttcc ggtcgactat    960

ggcagtggct aa                                                        972
```

```
<210> SEQ ID NO 22
<211> LENGTH: 323
<212> TYPE: PRT
<213> ORGANISM: Neosartorya fischeri

<400> SEQUENCE: 22

Met Ala Ser Met Asp Lys Val Phe Ser Gly Tyr His Ala Arg Gln Lys
1               5                   10                  15

Leu Leu Glu Arg Ser Asp Asn Pro Phe Ser Lys Gly Ile Ala Tyr Val
            20                  25                  30

Glu Gly Lys Leu Val Leu Pro Ser Asp Ala Arg Ile Pro Leu Leu Asp
        35                  40                  45

Glu Gly Phe Met His Gly Asp Leu Thr Tyr Asp Val Thr Thr Val Trp
    50                  55                  60

Asp Gly Arg Phe Phe Arg Leu Asp Asp His Met Gln Arg Ile Leu Glu
65                  70                  75                  80

Ser Cys Asp Lys Met Arg Leu Lys Phe Pro Leu Ala Pro Ser Thr Val
                85                  90                  95

Lys Asn Ile Leu Ala Glu Met Val Ala Lys Ser Gly Ile Arg Asp Ala
            100                 105                 110

Phe Val Glu Val Ile Val Thr Arg Gly Leu Thr Gly Val Arg Gly Ser
        115                 120                 125

Lys Pro Glu Asp Leu Tyr Asn Asn Asn Ile Tyr Leu Leu Val Leu Pro
    130                 135                 140

Tyr Val Trp Val Met Ala Pro Glu Asn Gln Leu Leu Gly Gly Ser Ala
145                 150                 155                 160

Ile Ile Thr Arg Thr Val Arg Arg Thr Pro Pro Gly Ala Phe Asp Pro
                165                 170                 175

Thr Ile Lys Asn Leu Gln Trp Gly Asp Leu Thr Lys Gly Leu Phe Glu
            180                 185                 190

Ala Met Asp Arg Gly Ala Thr Tyr Pro Phe Leu Thr Asp Gly Asp Thr
        195                 200                 205

Asn Leu Thr Glu Gly Ser Gly Phe Asn Ile Val Leu Val Lys Asn Gly
    210                 215                 220

Ile Ile Tyr Thr Pro Asp Arg Gly Val Leu Arg Gly Ile Thr Arg Lys
```

```
225                 230                 235                 240

Ser Val Ile Asp Val Ala Arg Ala Asn Asn Ile Asp Ile Arg Leu Glu
                245                 250                 255

Val Val Pro Val Glu Gln Val Tyr His Ser Asp Glu Ile Phe Met Cys
            260                 265                 270

Thr Thr Ala Gly Gly Ile Met Pro Ile Thr Leu Leu Asp Gly Gln Pro
        275                 280                 285

Val Asn Asp Gly Gln Val Gly Pro Ile Thr Lys Lys Ile Trp Asp Gly
    290                 295                 300

Tyr Trp Glu Met His Tyr Asn Pro Ala Tyr Ser Phe Pro Val Asp Tyr
305                 310                 315                 320

Gly Ser Gly
```

<210> SEQ ID NO 23
<211> LENGTH: 978
<212> TYPE: DNA
<213> ORGANISM: Gibberella zeae

<400> SEQUENCE: 23

```
atgtcgacca tggacaagat cttcgccggc cacgcccagc gccaagccac cctcgtcgca     60

agcgacaaca tcttcgccaa cggcattgcc tggatccaag gcgagctcgt ccccctcaat    120

gaagcccgca tccccctcat ggaccaaggt ttcatgcacg gcgacttgac ctacgatgtc    180

cctgcagtct gggatggtcg tttcttccgt cttgatgacc atctcgaccg tctcgaggca    240

agcgtcaaga agatgcgaat gcaattcccc attccccgcg atgagatcag aatgactctt    300

ctcgacatgc tcgccaagag tggaatcaag gatgcttttg ttgagctcat tgtcactcgt    360

ggcttgaagc ctgttcgtga ggccaagcct ggtgaggtct tgaacaacca cctctacttg    420

atcgtccaac cctacgtctg ggtcatgagc cccgaagctc agtacgtcgg cggtaatgcc    480

gttatcgcac gaactgttcg tcgaatccct cctggatcca tggatcccac catcaagaac    540

ctccaatgga gtgatttcac ccgcggcatg ttcgaagcat acgatcgtgg agcacaatac    600

cccttcctca ccgacggcga cacaaacatc accgaaggat ctggtttcaa cgttgtcttt    660

gtcaagaaca acgttattta caccccgaac cgaggagttt tgcagggaat taccagaaag    720

agtgtgatcg acgctgccaa gtggtgtggt catgaagttc gagtggagta tgtccctgtt    780

gagatggcct atgaagctga tgagatcttc atgtgtacta ctgctggagg aatcatgcct    840

atcaccacca tggatggaaa gccagtcaag gacggaaagg tcgggcctgt cacaaaggcc    900

atctgggatc ggtactgggc gatgcactgg gaggatgagt tcagtttcaa gattgactac    960

cagaaactga agctgtag                                                  978
```

<210> SEQ ID NO 24
<211> LENGTH: 325
<212> TYPE: PRT
<213> ORGANISM: Gibberella zeae

<400> SEQUENCE: 24

```
Met Ser Thr Met Asp Lys Ile Phe Ala Gly His Ala Gln Arg Gln Ala
1               5                   10                  15

Thr Leu Val Ala Ser Asp Asn Ile Phe Ala Asn Gly Ile Ala Trp Ile
            20                  25                  30

Gln Gly Glu Leu Val Pro Leu Asn Glu Ala Arg Ile Pro Leu Met Asp
        35                  40                  45

Gln Gly Phe Met His Gly Asp Leu Thr Tyr Asp Val Pro Ala Val Trp
    50                  55                  60
```

```
Asp Gly Arg Phe Phe Arg Leu Asp Asp His Leu Asp Arg Leu Glu Ala
65                  70                  75                  80

Ser Val Lys Lys Met Arg Met Gln Phe Pro Ile Pro Arg Asp Glu Ile
                85                  90                  95

Arg Met Thr Leu Leu Asp Met Leu Ala Lys Ser Gly Ile Lys Asp Ala
            100                 105                 110

Phe Val Glu Leu Ile Val Thr Arg Gly Leu Lys Pro Val Arg Glu Ala
        115                 120                 125

Lys Pro Gly Glu Val Leu Asn Asn His Leu Tyr Leu Ile Val Gln Pro
    130                 135                 140

Tyr Val Trp Val Met Ser Pro Glu Ala Gln Tyr Val Gly Gly Asn Ala
145                 150                 155                 160

Val Ile Ala Arg Thr Val Arg Arg Ile Pro Pro Gly Ser Met Asp Pro
                165                 170                 175

Thr Ile Lys Asn Leu Gln Trp Ser Asp Phe Thr Arg Gly Met Phe Glu
            180                 185                 190

Ala Tyr Asp Arg Gly Ala Gln Tyr Pro Phe Leu Thr Asp Gly Asp Thr
        195                 200                 205

Asn Ile Thr Glu Gly Ser Gly Phe Asn Val Val Phe Val Lys Asn Asn
    210                 215                 220

Val Ile Tyr Thr Pro Asn Arg Gly Val Leu Gln Gly Ile Thr Arg Lys
225                 230                 235                 240

Ser Val Ile Asp Ala Ala Lys Trp Cys Gly His Glu Val Arg Val Glu
                245                 250                 255

Tyr Val Pro Val Glu Met Ala Tyr Glu Ala Asp Glu Ile Phe Met Cys
            260                 265                 270

Thr Thr Ala Gly Gly Ile Met Pro Ile Thr Thr Met Asp Gly Lys Pro
        275                 280                 285

Val Lys Asp Gly Lys Val Gly Pro Val Thr Lys Ala Ile Trp Asp Arg
    290                 295                 300

Tyr Trp Ala Met His Trp Glu Asp Glu Phe Ser Phe Lys Ile Asp Tyr
305                 310                 315                 320

Gln Lys Leu Lys Leu
                325


<210> SEQ ID NO 25
<211> LENGTH: 966
<212> TYPE: DNA
<213> ORGANISM: Hyphomonas neptunium

<400> SEQUENCE: 25

atgctgacat ttcaaaaagt gctgaccgga tttcagacgc gggcagacgc tcgcgcagag      60

cgaacagacg cgttcgccga cggtattgcc tggatcgaaa acgaatttgt gcccatcgga     120

aaggcgcgga taccgatact tgatcagggc ttcctgcatt cggatctgac ctatgacgtc     180

cccgcagtct ggaatggccg gatcttccgt ctcgatgatc acctggaccg tctggaagtt     240

agctgcgcca aaatgcggct cccgctgccg atcgccaggc cagagctccg caggctggtg     300

atggagctgg tctccaggag tgggctgcgg gacgcatatg ttgagatcat cgtgacccgc     360

gggttgaagt tcctgcgagg cgcacaagcc gaagacatca tcccgaacct gtatctcatg     420

gcggtgcctt acgtctggat tctcccgctt gaataccaga accatggcgc gccggccgtc     480

gtaacgcgaa cggtgcgccg cacacccccg gggccctgg acccgacaat caagaacctt     540

cagtggggcg atctcgtccg agggcttatg gaagcaggtg accgggactc tttcttcccc     600
```

```
attcttcccg acggcgacgg gaacgccaca gaaggcgctg gctataatat cgtccttgtc    660

aggaatgggg aacttcacac accccgtcgc ggggtgctgg aaggcatcac acgcaggaca    720

gtactggaaa tagcggccgc gcgcggcctg aaaacacatg ttaccgagat acccatccag    780

gcactctatg aatgcgatga attgttcatg tgttcgacgg caggcggcat aatgccactc    840

gtccttctgg atgggaacat tgtgggtgat ggaacagtcg gtccggttac acggatgatt    900

tgggaggctt actgggatct tcatgatgat cctcagctca gcgagcctgt gacttacgcg    960

ccctga                                                               966


<210> SEQ ID NO 26
<211> LENGTH: 321
<212> TYPE: PRT
<213> ORGANISM: Hyphonmonas neptunium

<400> SEQUENCE: 26

Met Leu Thr Phe Gln Lys Val Leu Thr Gly Phe Gln Thr Arg Ala Asp
1               5                   10                  15

Ala Arg Ala Glu Arg Thr Asp Ala Phe Ala Asp Gly Ile Ala Trp Ile
            20                  25                  30

Glu Asn Glu Phe Val Pro Ile Gly Lys Ala Arg Ile Pro Ile Leu Asp
        35                  40                  45

Gln Gly Phe Leu His Ser Asp Leu Thr Tyr Asp Val Pro Ala Val Trp
    50                  55                  60

Asn Gly Arg Ile Phe Arg Leu Asp Asp His Leu Asp Arg Leu Glu Val
65                  70                  75                  80

Ser Cys Ala Lys Met Arg Leu Pro Leu Pro Ile Ala Arg Pro Glu Leu
                85                  90                  95

Arg Arg Leu Val Met Glu Leu Val Ser Arg Ser Gly Leu Arg Asp Ala
            100                 105                 110

Tyr Val Glu Ile Ile Val Thr Arg Gly Leu Lys Phe Leu Arg Gly Ala
        115                 120                 125

Gln Ala Glu Asp Ile Ile Pro Asn Leu Tyr Leu Met Ala Val Pro Tyr
    130                 135                 140

Val Trp Ile Leu Pro Leu Glu Tyr Gln Asn His Gly Ala Pro Ala Val
145                 150                 155                 160

Val Thr Arg Thr Val Arg Arg Thr Pro Pro Gly Ala Leu Asp Pro Thr
                165                 170                 175

Ile Lys Asn Leu Gln Trp Gly Asp Leu Val Arg Gly Leu Met Glu Ala
            180                 185                 190

Gly Asp Arg Asp Ser Phe Phe Pro Ile Leu Pro Asp Gly Asp Gly Asn
        195                 200                 205

Ala Thr Glu Gly Ala Gly Tyr Asn Ile Val Leu Val Arg Asn Gly Glu
    210                 215                 220

Leu His Thr Pro Arg Arg Gly Val Leu Glu Gly Ile Thr Arg Arg Thr
225                 230                 235                 240

Val Leu Glu Ile Ala Ala Ala Arg Gly Leu Lys Thr His Val Thr Glu
                245                 250                 255

Ile Pro Ile Gln Ala Leu Tyr Glu Cys Asp Glu Leu Phe Met Cys Ser
            260                 265                 270

Thr Ala Gly Gly Ile Met Pro Leu Val Leu Leu Asp Gly Asn Ile Val
        275                 280                 285

Gly Asp Gly Thr Val Gly Pro Val Thr Arg Met Ile Trp Glu Ala Tyr
    290                 295                 300

Trp Asp Leu His Asp Asp Pro Gln Leu Ser Glu Pro Val Thr Tyr Ala
```

305 310 315 320

Pro

<210> SEQ ID NO 27
<211> LENGTH: 963
<212> TYPE: DNA
<213> ORGANISM: Mesorhizobium loti MAFF303099

<400> SEQUENCE: 27

```
atggaccaga cgacggcaac acaggcttca aagccgctgc ccacagtcgg cgaccgccac     60
gtcgacccgc attcctaccc cgacggcatc gccttcctcg acggccagta tctgccgatg    120
tcgcaagcca aggtgtcggt gctggactgg ggcttcctgc attccgacgc cacctacgac    180
acggtgcatg tctggaacgg ccgcttcttc cgcctcgacc tgcatctcga ccgcttcttc    240
ggcggactgg aaaagctgcg catgaccatc cccttcgaca gggatggcgt ggccgagatc    300
ctgcacaatt gtgtcgccct ttcgggccat cgcgccgcct atgtcgaaat gctgtgcacg    360
cgcggcgcat cgccgacctt cagccgcgat ccgcgccagg cgatcaaccg cttcatggcc    420
ttcgccgtac ccttcggctc ggtcgccaat gccgagcagt tgcagcgcgg cctgcgcgtc    480
gccatcagcg acaaggtgcg catcccgccg gcttcggtcg atccgtcgat caagaactac    540
cattggctcg atctggtgcg cggcctctac gacgcctatg acagcggtgc ggagaccgcg    600
ctcattctcg acttcaacgg caatgtcgcc gagggcccgg gcttcaacgt cttctgcgtc    660
aaggacggca aactgtcgac gccggccatc ggcgtgctgc ccggcatcac gcgccgcaca    720
gtcttcgatc tctgcgccga agaaggtctt gccgccgccg ccgccgatgt cagcgtcgcc    780
gcgctcaagg cggccgacga ggtcttcatc acctcgaccg ccggcggcat catgccggtg    840
accgagatcg acggcgcggc gatcgccgac ggcaaggtcg ggccggttac cagccggcta    900
atggcgctct actggcaaaa gcacgacgat ccggcctggt cgtctcaggt gaagtatccc    960
tga                                                                  963
```

<210> SEQ ID NO 28
<211> LENGTH: 320
<212> TYPE: PRT
<213> ORGANISM: Mesorhizobium loti MAFF303099

<400> SEQUENCE: 28

```
Met Asp Gln Thr Thr Ala Thr Gln Ala Ser Lys Pro Leu Pro Thr Val
1               5                   10                  15

Gly Asp Arg His Val Asp Pro His Ser Tyr Pro Asp Gly Ile Ala Phe
            20                  25                  30

Leu Asp Gly Gln Tyr Leu Pro Met Ser Gln Ala Lys Val Ser Val Leu
        35                  40                  45

Asp Trp Gly Phe Leu His Ser Asp Ala Thr Tyr Asp Thr Val His Val
    50                  55                  60

Trp Asn Gly Arg Phe Phe Arg Leu Asp Leu His Leu Asp Arg Phe Phe
65                  70                  75                  80

Gly Gly Leu Glu Lys Leu Arg Met Thr Ile Pro Phe Asp Arg Asp Gly
                85                  90                  95

Val Ala Glu Ile Leu His Asn Cys Val Ala Leu Ser Gly His Arg Ala
            100                 105                 110

Ala Tyr Val Glu Met Leu Cys Thr Arg Gly Ala Ser Pro Thr Phe Ser
        115                 120                 125

Arg Asp Pro Arg Gln Ala Ile Asn Arg Phe Met Ala Phe Ala Val Pro
    130                 135                 140
```

```
Phe Gly Ser Val Ala Asn Ala Glu Gln Leu Gln Arg Gly Leu Arg Val
145                 150                 155                 160

Ala Ile Ser Asp Lys Val Arg Ile Pro Pro Ala Ser Val Asp Pro Ser
                165                 170                 175

Ile Lys Asn Tyr His Trp Leu Asp Leu Val Arg Gly Leu Tyr Asp Ala
            180                 185                 190

Tyr Asp Ser Gly Ala Glu Thr Ala Leu Ile Leu Asp Phe Asn Gly Asn
        195                 200                 205

Val Ala Glu Gly Pro Gly Phe Asn Val Phe Cys Val Lys Asp Gly Lys
    210                 215                 220

Leu Ser Thr Pro Ala Ile Gly Val Leu Pro Gly Ile Thr Arg Arg Thr
225                 230                 235                 240

Val Phe Asp Leu Cys Ala Glu Glu Gly Leu Ala Ala Ala Ala Ala Asp
                245                 250                 255

Val Ser Val Ala Ala Leu Lys Ala Ala Asp Glu Val Phe Ile Thr Ser
            260                 265                 270

Thr Ala Gly Gly Ile Met Pro Val Thr Glu Ile Asp Gly Ala Ala Ile
        275                 280                 285

Ala Asp Gly Lys Val Gly Pro Val Thr Ser Arg Leu Met Ala Leu Tyr
    290                 295                 300

Trp Gln Lys His Asp Asp Pro Ala Trp Ser Ser Gln Val Lys Tyr Pro
305                 310                 315                 320
```

<210> SEQ ID NO 29
<211> LENGTH: 936
<212> TYPE: DNA
<213> ORGANISM: Roseobacter sp.

<400> SEQUENCE: 29

```
tcaaggatat cggatcgctt tccgaaaacg atcatcttca tgcatcctcc aatacgcttc     60

agtgatctcc ttggttatcg ggccgaccaa tccgcttcca attgaagttt catcgatctt    120

ggtgacgggc atgacgccgc cagcggttga ggtcacgaac acttcatccg ccgccctcaa    180

ttcacttggt gccagatcat ccgtcgcgca ggtgatctgt aattcgtcac aaagatcaaa    240

gattgtttgg cgtgttattc ccatcagcac cccaaacttg ggcgaggaaa ttttgccgtt    300

tttcacggcg aagacgttga aaccgggccc ttccgctatg tttccggtgg cgtctaaaag    360

aatggcggtt tcggctccct gcgcatacgc cgcatacaaa cctttgacca ggtccagcca    420

gtgatagttc tttacggttg gatcaacgga gctgggtgga atgcggacaa ggtcggtgac    480

ggctgcgtgt aagccacgtc tcatctgttc tgggtttgca accgacccaa atggaattgc    540

gaaggcgatg aagcggttga cggcatcgcg agggtcgcgg ctaaacgtag gagaagtgcc    600

gcgtgtgcag atgaactcga catacgcatc ctggagacct gatagagcaa cgcaattgtg    660

caaaatctca gtcatctcgg cacgaccaaa cgggatcgac atgtgcaact tttccatccc    720

tgcgaagaac cggtcaagat gatcatcaag cctgaaaaat gctcccttcc acacatgcgc    780

aacatcgtat gtcgcatctg agtggaggaa gccattatcc aacaccgaaa tctttgcctc    840

gctgatcgga agatattggc catccatgaa ggcaatgccg ggagggtacg ttgccgggtc    900

agaatgacga tcagacagcg caggcaattt atacat                                936
```

<210> SEQ ID NO 30
<211> LENGTH: 311
<212> TYPE: PRT
<213> ORGANISM: Roseobacter sp.

<400> SEQUENCE: 30

```
Met Tyr Lys Leu Pro Ala Leu Ser Asp Arg His Ser Asp Pro Ala Thr
1               5                   10                  15

Tyr Pro Pro Gly Ile Ala Phe Met Asp Gly Gln Tyr Leu Pro Ile Ser
            20                  25                  30

Glu Ala Lys Ile Ser Val Leu Asp Asn Gly Phe Leu His Ser Asp Ala
        35                  40                  45

Thr Tyr Asp Val Ala His Val Trp Lys Gly Ala Phe Phe Arg Leu Asp
    50                  55                  60

Asp His Leu Asp Arg Phe Phe Ala Gly Met Glu Lys Leu His Met Ser
65                  70                  75                  80

Ile Pro Phe Gly Arg Ala Glu Met Thr Glu Ile Leu His Asn Cys Val
                85                  90                  95

Ala Leu Ser Gly Leu Gln Asp Ala Tyr Val Glu Phe Ile Cys Thr Arg
            100                 105                 110

Gly Thr Ser Pro Thr Phe Ser Arg Asp Pro Arg Asp Ala Val Asn Arg
        115                 120                 125

Phe Ile Ala Phe Ala Ile Pro Phe Gly Ser Val Ala Asn Pro Glu Gln
    130                 135                 140

Met Arg Arg Gly Leu His Ala Ala Val Thr Asp Leu Val Arg Ile Pro
145                 150                 155                 160

Pro Ser Ser Val Asp Pro Thr Val Lys Asn Tyr His Trp Leu Asp Leu
                165                 170                 175

Val Lys Gly Leu Tyr Ala Ala Tyr Ala Gln Gly Ala Glu Thr Ala Ile
            180                 185                 190

Leu Leu Asp Ala Thr Gly Asn Ile Ala Glu Gly Pro Gly Phe Asn Val
        195                 200                 205

Phe Ala Val Lys Asn Gly Lys Ile Ser Ser Pro Lys Phe Gly Val Leu
    210                 215                 220

Met Gly Ile Thr Arg Gln Thr Ile Phe Asp Leu Cys Asp Glu Leu Gln
225                 230                 235                 240

Ile Thr Cys Ala Thr Asp Asp Leu Ala Pro Ser Glu Leu Arg Ala Ala
                245                 250                 255

Asp Glu Val Phe Val Thr Ser Thr Ala Gly Gly Val Met Pro Val Thr
            260                 265                 270

Lys Ile Asp Glu Thr Ser Ile Gly Ser Gly Leu Val Gly Pro Ile Thr
        275                 280                 285

Lys Glu Ile Thr Glu Ala Tyr Trp Arg Met His Glu Asp Asp Arg Phe
    290                 295                 300

Arg Lys Ala Ile Arg Tyr Pro
305                 310
```

<210> SEQ ID NO 31
<211> LENGTH: 945
<212> TYPE: DNA
<213> ORGANISM: Marinomonas sp.

<400> SEQUENCE: 31

```
ctatattttt gccgggggat aatgaatggg taggcaccaa tcagagtttt tgtgcttttc      60

ccaatatgca gattttaaca attggaagat aggtccggtt gtgccacttc caatcacatt     120

atggtcgatt ttggtaatgg gcataatgcc acccgccgtt gacgtaatga atacttcgtc     180

agcattcctt aaatcggtag gcgttacctc agttgcacag cagcttatgt gtaattcgtc     240

acaaagatca aagacggttc ggcgagttat gcctggcaaa acccctttt ctggtgttgt      300
```

```
aattatcttt cccttaacac aaaaaacatt aaagccaggg ccttcggcga tattaccctc    360

tgaatccaac aggatggcgg tctcaccacc tttttcatag gcatcgtata acccggttac    420

caaatcaagc caatggtaat ttttgacctt tgaatcaacc gagtttggcg gaatacggac    480

aatagagcta ataatggcat gcagtccatt tttcatttga tcttgatttg cgaccgagcc    540

aaagggaacg gcgaaagcca taaaacgatt gattgagtct cttgggtccc ggctgaaatc    600

cggcgaattc cctcttgtgc atatcatttc gacataggcg tttttatgac ccgataaggc    660

cacgcaatta tgcaaaattt cagcgacctc ttctttggag taaggcattg tcatatgaat    720

tttctctaac cctgagaaaa aacgttcaag gtacaaatcc aacctgaaaa atgcaccttg    780

ccagacatgg acaacatcat aggttgcgtc agaatgcaaa aagccataat caagaatgga    840

tagttttgct tttgacatat ctaaatattg accatccatg taggcgacgc cttttggata    900

attatgtggg tccttatatt cattggacaa ttgcagtaaa gccat                    945
```

<210> SEQ ID NO 32
<211> LENGTH: 314
<212> TYPE: PRT
<213> ORGANISM: Marinomonas sp.

<400> SEQUENCE: 32

```
Met Ala Leu Leu Gln Leu Ser Asn Glu Tyr Lys Asp Pro His Asn Tyr
1               5                   10                  15

Pro Lys Gly Val Ala Tyr Met Asp Gly Gln Tyr Leu Asp Met Ser Lys
            20                  25                  30

Ala Lys Leu Ser Ile Leu Asp Tyr Gly Phe Leu His Ser Asp Ala Thr
        35                  40                  45

Tyr Asp Val Val His Val Trp Gln Gly Ala Phe Phe Arg Leu Asp Leu
    50                  55                  60

Tyr Leu Glu Arg Phe Phe Ser Gly Leu Glu Lys Ile His Met Thr Met
65                  70                  75                  80

Pro Tyr Ser Lys Glu Glu Val Ala Glu Ile Leu His Asn Cys Val Ala
                85                  90                  95

Leu Ser Gly His Lys Asn Ala Tyr Val Glu Met Ile Cys Thr Arg Gly
            100                 105                 110

Asn Ser Pro Asp Phe Ser Arg Asp Pro Arg Asp Ser Ile Asn Arg Phe
        115                 120                 125

Met Ala Phe Ala Val Pro Phe Gly Ser Val Ala Asn Gln Asp Gln Met
    130                 135                 140

Lys Asn Gly Leu His Ala Ile Ile Ser Ser Ile Val Arg Ile Pro Pro
145                 150                 155                 160

Asn Ser Val Asp Ser Lys Val Lys Asn Tyr His Trp Leu Asp Leu Val
                165                 170                 175

Thr Gly Leu Tyr Asp Ala Tyr Glu Lys Gly Gly Glu Thr Ala Ile Leu
            180                 185                 190

Leu Asp Ser Glu Gly Asn Ile Ala Glu Gly Pro Gly Phe Asn Val Phe
        195                 200                 205

Cys Val Lys Gly Lys Ile Ile Thr Thr Pro Glu Lys Gly Val Leu Pro
    210                 215                 220

Gly Ile Thr Arg Arg Thr Val Phe Asp Leu Cys Asp Glu Leu His Ile
225                 230                 235                 240

Ser Cys Cys Ala Thr Glu Val Thr Pro Thr Asp Leu Arg Asn Ala Asp
                245                 250                 255

Glu Val Phe Ile Thr Ser Thr Ala Gly Gly Ile Met Pro Ile Thr Lys
            260                 265                 270
```

```
Ile Asp His Asn Val Ile Gly Ser Gly Thr Thr Gly Pro Ile Phe Gln
        275                 280                 285

Leu Leu Lys Ser Ala Tyr Trp Glu Lys His Lys Asn Ser Asp Trp Cys
    290                 295                 300

Leu Pro Ile His Tyr Pro Pro Ala Lys Ile
305                 310


<210> SEQ ID NO 33
<211> LENGTH: 939
<212> TYPE: DNA
<213> ORGANISM: Rhizobium etli

<400> SEQUENCE: 33

gtgctcgatc gcggcgagga atccgccttt cagaaaggct ccgcctatgt cgatggaaaa      60

attataccaa tcgaagaggc gaaggtacca cttttagact ggggctttct gcgttcggac     120

gcgtgtcagg acacagtgtc ggtgtgggat ggcagctttt tccgtttgac tgaccacctg     180

gatcgatttg agcgatctgt ccagcgcctt cggatggata cagctcctgt tacaagaagc     240

gatatccacc ggatagtcca caaactcgtt gccgtgtgcg gtttccgtga tgcttacgtt     300

caaatcatca tgacccgcgg gcggcccccg atcggtagtc gggatcttcg tttatgctcg     360

aacagcttcc aggcattctg cgtgccgtac atgtggatcg cgaaccccga aaagcaggaa     420

attggcatgg cagtgcacgt cagccggcgc gtccgaatcc cacctcagtc cgtagatccg     480

ttggtgaagc attaccattg gctcgacttt gagatgggct tgttcgaagc ttacgagaac     540

ggtgccgata cggtggttct cactgatctc gatggcaata tcacagaggg gcccggcttc     600

aacgttttcg cggtgatcga cggagttctg aggacccctt ctttcggcat gctggatgga     660

atgaccagga ggacagttat ggaactgtgc aacgagctga atctcgatgt cacgcaagag     720

accatttctt tggagcggct tctaatcgcc tcggaaatct tccttacgac gaccgcaggc     780

gggattatcc cggtctcttc ggtgaacgga accggaatcg gtttcggatc agtgggtgaa     840

caaactcgcc gcattcaccg gtcatactgg gataagcgaa gcagcggatg gtatggcgag     900

cctgtcgcct acgcccaaaa agctctcttg gagccctag                            939


<210> SEQ ID NO 34
<211> LENGTH: 312
<212> TYPE: PRT
<213> ORGANISM: Rhizobium etli

<400> SEQUENCE: 34

Met Leu Asp Arg Gly Glu Glu Ser Ala Phe Gln Lys Gly Ser Ala Tyr
1               5                   10                  15

Val Asp Gly Lys Ile Ile Pro Ile Glu Glu Ala Lys Val Pro Leu Leu
            20                  25                  30

Asp Trp Gly Phe Leu Arg Ser Asp Ala Cys Gln Asp Thr Val Ser Val
        35                  40                  45

Trp Asp Gly Ser Phe Phe Arg Leu Thr Asp His Leu Asp Arg Phe Glu
    50                  55                  60

Arg Ser Val Gln Arg Leu Arg Met Asp Thr Ala Pro Val Thr Arg Ser
65                  70                  75                  80

Asp Ile His Arg Ile Val His Lys Leu Val Ala Val Cys Gly Phe Arg
                85                  90                  95

Asp Ala Tyr Val Gln Ile Ile Met Thr Arg Gly Arg Pro Pro Ile Gly
            100                 105                 110

Ser Arg Asp Leu Arg Leu Cys Ser Asn Ser Phe Gln Ala Phe Cys Val
```

```
        115                 120                 125

Pro Tyr Met Trp Ile Ala Asn Pro Glu Lys Gln Glu Ile Gly Met Ala
    130                 135                 140

Val His Val Ser Arg Arg Val Arg Ile Pro Pro Gln Ser Val Asp Pro
145                 150                 155                 160

Leu Val Lys His Tyr His Trp Leu Asp Phe Glu Met Gly Leu Phe Glu
                165                 170                 175

Ala Tyr Glu Asn Gly Ala Asp Thr Val Val Leu Thr Asp Leu Asp Gly
            180                 185                 190

Asn Ile Thr Glu Gly Pro Gly Phe Asn Val Phe Ala Val Ile Asp Gly
        195                 200                 205

Val Leu Arg Thr Pro Ser Phe Gly Met Leu Asp Gly Met Thr Arg Arg
    210                 215                 220

Thr Val Met Glu Leu Cys Asn Glu Leu Asn Leu Asp Val Thr Gln Glu
225                 230                 235                 240

Thr Ile Ser Leu Glu Arg Leu Leu Ile Ala Ser Glu Ile Phe Leu Thr
                245                 250                 255

Thr Thr Ala Gly Gly Ile Ile Pro Val Ser Ser Val Asn Gly Thr Gly
            260                 265                 270

Ile Gly Phe Gly Ser Val Gly Glu Gln Thr Arg Arg Ile His Arg Ser
        275                 280                 285

Tyr Trp Asp Lys Arg Ser Ser Gly Trp Tyr Gly Glu Pro Val Ala Tyr
    290                 295                 300

Ala Gln Lys Ala Leu Leu Glu Pro
305                 310


<210> SEQ ID NO 35
<211> LENGTH: 906
<212> TYPE: DNA
<213> ORGANISM: Rhodoferax ferrireducens

<400> SEQUENCE: 35

atgccagcac ccgatctttc caaaggcgtc gcctttgtac gtgggcagta cgtccccatt      60

ggtgaagcaa gcattccgat aactgactgg ggtttcctgc gctctgacgc cacctatgac     120

gtggtgacgg tgtgggatgg ttcctttttt cgcctggacg cccatctgga gcgcttcatg     180

cgcagctgcc aacgctggcg gcttgacccg gggctgacgc ccgggcaaat caccggcgtg     240

ttgtcgcaat gcgtgcgcct gagcgggctt cgcgcctctt atgtcgagat gatctgcacc     300

cggggccagc cgccttgggg atcgcgcgac ccacgcctgg ccgtcaatca gttctatgcc     360

tttgcggtgc cctatgtctg gcttgccaat gcccagcagc gtgaagcggg actgcacctg     420

atgatcagcg acgtgcaacg tattcctgcg acctccgtgg acccttcggc caagaactac     480

cactggaacg acttgacgat gggactgctg gggcgctgg acgccggggc cgacagtgtt      540

gtgctggtcg actcagtcgg gaacgtggtc gagggacccg ggttcaacgt gttttgtgtc     600

agccacggcg cgcttgtgac gcccagcgag ggcatgcttg aaggggtgtc gcgtcgcacc     660

gtcatcgaga tggcgcgcgc tctggggctg gagacacaac tgcgtgcctt gcccgccgat     720

gagttgcgtg gagccgagga ggtgttcatc tccacctcgg gcggtggtgt actgcccgtg     780

agccgggtgg acaaacgtcc ggttggtgat ggccgtccgg ggccgatcac gcagcgcctg     840

gtacagacct actgggcctg gcatgccgat ccggtgtaca gccagccgat agattattcg     900

ctttga                                                                906


<210> SEQ ID NO 36
```

<211> LENGTH: 301
<212> TYPE: PRT
<213> ORGANISM: Rhodoferax ferrireducens

<400> SEQUENCE: 36

```
Met Pro Ala Pro Asp Leu Ser Lys Gly Val Ala Phe Val Arg Gly Gln
1               5                   10                  15

Tyr Val Pro Ile Gly Glu Ala Ser Ile Pro Ile Thr Asp Trp Gly Phe
            20                  25                  30

Leu Arg Ser Asp Ala Thr Tyr Asp Val Val Thr Val Trp Asp Gly Ser
        35                  40                  45

Phe Phe Arg Leu Asp Ala His Leu Glu Arg Phe Met Arg Ser Cys Gln
    50                  55                  60

Arg Trp Arg Leu Asp Pro Gly Leu Thr Pro Gly Gln Ile Thr Gly Val
65                  70                  75                  80

Leu Ser Gln Cys Val Arg Leu Ser Gly Leu Arg Ala Ser Tyr Val Glu
                85                  90                  95

Met Ile Cys Thr Arg Gly Gln Pro Pro Trp Gly Ser Arg Asp Pro Arg
            100                 105                 110

Leu Ala Val Asn Gln Phe Tyr Ala Phe Ala Val Pro Tyr Val Trp Leu
        115                 120                 125

Ala Asn Ala Gln Gln Arg Glu Ala Gly Leu His Leu Met Ile Ser Asp
    130                 135                 140

Val Gln Arg Ile Pro Ala Thr Ser Val Asp Pro Ser Ala Lys Asn Tyr
145                 150                 155                 160

His Trp Asn Asp Leu Thr Met Gly Leu Leu Gly Ala Leu Asp Ala Gly
                165                 170                 175

Ala Asp Ser Val Val Leu Val Asp Ser Val Gly Asn Val Val Glu Gly
            180                 185                 190

Pro Gly Phe Asn Val Phe Cys Val Ser His Gly Ala Leu Val Thr Pro
        195                 200                 205

Ser Glu Gly Met Leu Glu Gly Val Ser Arg Arg Thr Val Ile Glu Met
    210                 215                 220

Ala Arg Ala Leu Gly Leu Glu Thr Gln Leu Arg Ala Leu Pro Ala Asp
225                 230                 235                 240

Glu Leu Arg Gly Ala Glu Glu Val Phe Ile Ser Thr Ser Gly Gly Gly
                245                 250                 255

Val Leu Pro Val Ser Arg Val Asp Lys Arg Pro Val Gly Asp Gly Arg
            260                 265                 270

Pro Gly Pro Ile Thr Gln Arg Leu Val Gln Thr Tyr Trp Ala Trp His
        275                 280                 285

Ala Asp Pro Val Tyr Ser Gln Pro Ile Asp Tyr Ser Leu
    290                 295                 300
```

<210> SEQ ID NO 37
<211> LENGTH: 900
<212> TYPE: DNA
<213> ORGANISM: Jannaschia sp.

<400> SEQUENCE: 37

```
tcaataggcg atgtcggttc ggtgctcggc ccgcgtgatc cagtcgaaat accgccgccg     60

caggtccagc gccacgggcc ctgccgcatc gttggagaag acgcggttat cgacccgcgc    120

caccgggatc acgccgccgc ccgaggacga caggaagacc tcatcggcct ccaggaattc    180

gtccaggggc agcgggcgtg tttcgaccgt caggcccgcc tctgcggcca tttccagcac    240

cgtgcggcgg gtgatgccat gcaacacacc gtggtccgac gtcacgatcc ggtcaccgaa    300
```

```
cagggcgaag gcgttgaagc ccggcccttc ggtcacatgg cccgcgtggt ccagcagcaa    360

gaccgtctca aaccccttgt ctttcgcctc gaacaacccg ccggtgaaat cgccccaatg    420

gtagtttttc acggtgggat caacgctgtc ggcggggatg cggcgggtgc gtttggcgat    480

ccagacggag gttccacgct cggcgatttc gggtttcacg atgtgcacgt acggcacgca    540

ccaggcgtag aagtggttgg cacaatcgcg cgggtcccgc gatccgggca ccgggttgcg    600

cccccgcgcg gcgaccatgg cgacatagct gtcgcgcaat ccgcttgcgg ccaccatccg    660

ggtcagggcc gttttcacgc cgtccccgtc gcgcccgata tccatccgca gcgcgccgac    720

ggaggccatg aaccgcgcca cgtaatcatc cagccggaag aagccgcccc gccagaccgg    780

caccacgtca taggcgatgt cggaatgggt caggccccaa tcggtgacgg ggatcgcggc    840

ctctgcgatg gggatgatgc ggctccccat ccaggccgcg ccgttggata aatcattcat    900
```

<210> SEQ ID NO 38
<211> LENGTH: 299
<212> TYPE: PRT
<213> ORGANISM: Jannaschia sp.

<400> SEQUENCE: 38

```
Met Asn Asp Leu Ser Asn Gly Ala Ala Trp Met Gly Ser Arg Ile Ile
1               5                   10                  15

Pro Ile Ala Glu Ala Ala Ile Pro Val Thr Asp Trp Gly Leu Thr His
            20                  25                  30

Ser Asp Ile Ala Tyr Asp Val Val Pro Val Trp Arg Gly Gly Phe Phe
        35                  40                  45

Arg Leu Asp Asp Tyr Val Ala Arg Phe Met Ala Ser Val Gly Ala Leu
    50                  55                  60

Arg Met Asp Ile Gly Arg Asp Gly Asp Gly Val Lys Thr Ala Leu Thr
65                  70                  75                  80

Arg Met Val Ala Ala Ser Gly Leu Arg Asp Ser Tyr Val Ala Met Val
                85                  90                  95

Ala Ala Arg Gly Arg Asn Pro Val Pro Gly Ser Arg Asp Pro Arg Asp
            100                 105                 110

Cys Ala Asn His Phe Tyr Ala Trp Cys Val Pro Tyr Val His Ile Val
        115                 120                 125

Lys Pro Glu Ile Ala Glu Arg Gly Thr Ser Val Trp Ile Ala Lys Arg
    130                 135                 140

Thr Arg Arg Ile Pro Ala Asp Ser Val Asp Pro Thr Val Lys Asn Tyr
145                 150                 155                 160

His Trp Gly Asp Phe Thr Gly Gly Leu Phe Glu Ala Lys Asp Lys Gly
                165                 170                 175

Phe Glu Thr Val Leu Leu Leu Asp His Ala Gly His Val Thr Glu Gly
            180                 185                 190

Pro Gly Phe Asn Ala Phe Ala Leu Phe Gly Asp Arg Ile Val Thr Ser
        195                 200                 205

Asp His Gly Val Leu His Gly Ile Thr Arg Arg Thr Val Leu Glu Met
    210                 215                 220

Ala Ala Glu Ala Gly Leu Thr Val Glu Thr Arg Pro Leu Pro Leu Asp
225                 230                 235                 240

Glu Phe Leu Glu Ala Asp Glu Val Phe Leu Ser Ser Ser Gly Gly Gly
                245                 250                 255

Val Ile Pro Val Ala Arg Val Asp Asn Arg Val Phe Ser Asn Asp Ala
            260                 265                 270
```

```
Ala Gly Pro Val Ala Leu Asp Leu Arg Arg Arg Tyr Phe Asp Trp Ile
        275                 280                 285

Thr Arg Ala Glu His Arg Thr Asp Ile Ala Tyr
    290                 295


<210> SEQ ID NO 39
<211> LENGTH: 936
<212> TYPE: DNA
<213> ORGANISM: Labrenzia alexandrii

<400> SEQUENCE: 39

ctaatcccga taagaaatct ccgtccggtt atccggacgg gcggcccatt caaaataggc      60

cttgtgaagt gctgtcgtaa tcggacccgg cgcatcattt gaaaagatcc ggtcatccac     120

ccgggtgacc ggtgcaacgc cgccaccgga cgtggtgatg aaaacttcgt cgctctcaaa     180

gaactcacta agcgccaagg cccgtatctc gatctcaagc ccctgttctg ccgcgatatc     240

cagcaccgtc tgacggctga tgccttccaa aacaccgctt tcagccgtca ccagcgttcg     300

gccctttaca gcaaacacat tgaagcccgg cccttcggtc acgttgccat catcatcgag     360

caagatgaca gtctccgcgc cgtggtcctt ggcctcaaac agacccttgg tgaaatcacc     420

ccagtggtag tttttgacct tcggattgac actgccgggc gaaatccggt gcacggtctt     480

ggcgatatga acatgggcgc ctctttccgc gatctccggc cggatgacgt gaacataggg     540

cacgcaccat gcaaagaatt ggttcttgca gtcccgggga tcgcgcgaac ccggcacctg     600

gttcacaccc cgggaagtga ccattgccac gtaggccttt cgcagccccg tcgccgccac     660

gagcgattga agggcgtctt ccatctcctc atcgctcaac ccagggtcca accgcagttc     720

gtccatcgag cggcggaaac gggccagata atggggcaaa cgaaagaatg caccatccaa     780

gaccgggacc acatcatagg taatgtccga atggatcagc cccaatctg taacaggcaa     840

tgcggcctcg gaaatcggca tgagcctgcc gcccatccac gcggcaccgt tggacaaatc     900

tgagatggta acgcgaacat cgacggtgga ggacat                               936


<210> SEQ ID NO 40
<211> LENGTH: 311
<212> TYPE: PRT
<213> ORGANISM: Labrenzia alexandrii

<400> SEQUENCE: 40

Met Ser Ser Thr Val Asp Val Arg Val Thr Ile Ser Asp Leu Ser Asn
1               5                   10                  15

Gly Ala Ala Trp Met Gly Gly Arg Leu Met Pro Ile Ser Glu Ala Ala
            20                  25                  30

Leu Pro Val Thr Asp Trp Gly Leu Ile His Ser Asp Ile Thr Tyr Asp
        35                  40                  45

Val Val Pro Val Leu Asp Gly Ala Phe Phe Arg Leu Pro His Tyr Leu
    50                  55                  60

Ala Arg Phe Arg Arg Ser Met Asp Glu Leu Arg Leu Asp Pro Gly Leu
65                  70                  75                  80

Ser Asp Glu Glu Met Glu Asp Ala Leu Gln Ser Leu Val Ala Ala Thr
                85                  90                  95

Gly Leu Arg Lys Ala Tyr Val Ala Met Val Thr Ser Arg Gly Val Asn
            100                 105                 110

Gln Val Pro Gly Ser Arg Asp Pro Arg Asp Cys Lys Asn Gln Phe Phe
        115                 120                 125

Ala Trp Cys Val Pro Tyr Val His Val Ile Arg Pro Glu Ile Ala Glu
    130                 135                 140
```

```
Arg Gly Ala His Val His Ile Ala Lys Thr Val His Arg Ile Ser Pro
145                 150                 155                 160

Gly Ser Val Asn Pro Lys Val Lys Asn Tyr His Trp Gly Asp Phe Thr
                165                 170                 175

Lys Gly Leu Phe Glu Ala Lys Asp His Gly Ala Glu Thr Val Ile Leu
            180                 185                 190

Leu Asp Asp Asp Gly Asn Val Thr Glu Gly Pro Gly Phe Asn Val Phe
        195                 200                 205

Ala Val Lys Gly Arg Thr Leu Val Thr Ala Glu Ser Gly Val Leu Glu
    210                 215                 220

Gly Ile Ser Arg Gln Thr Val Leu Asp Ile Ala Ala Glu Gln Gly Leu
225                 230                 235                 240

Glu Ile Glu Ile Arg Ala Leu Ala Leu Ser Glu Phe Phe Glu Ser Asp
                245                 250                 255

Glu Val Phe Ile Thr Thr Ser Gly Gly Gly Val Ala Pro Val Thr Arg
            260                 265                 270

Val Asp Asp Arg Ile Phe Ser Asn Asp Ala Pro Gly Pro Ile Thr Thr
        275                 280                 285

Ala Leu His Lys Ala Tyr Phe Glu Trp Ala Ala Arg Pro Asp Asn Arg
    290                 295                 300

Thr Glu Ile Ser Tyr Arg Asp
305                 310
```

<210> SEQ ID NO 41
<211> LENGTH: 981
<212> TYPE: DNA
<213> ORGANISM: Burkholderia sp.

<400> SEQUENCE: 41

```
ttatgccggg accgacgaga agtattcagc cggctgcgcg tgccatcctg cccagcgctt      60

ctcccagtag aggttgtgaa tcttctcgga gatcgggccg gggccgttgc ggttgccgag     120

cggctgatcg tcgattgcgc tgacgggcat gatcccgcct gccgacgacg aggtgaatgc     180

ttcgtcagcc tcgcgcagct gggtcgcggt gtacttgccg atgttcacct tgatgccgag     240

ctcggcggcg atatcgaaga cgctctggcg cgtgatgccc agcaggcagc cttcggcggg     300

cgtatagagc tccccgttct tggcgaaaaa cacgttcgca ccggctgctt cggtgaggtt     360

gtcgctttcg tcgacgagaa ccgcccagtc cttctcctgc gtcatggctt cgaacagcgc     420

gagcttcatg tccatccagt ggaagttctt ggccgtggga tcgaccgcct tcgcggaaat     480

gcggttgtac agcttgctga tcagcaggtt cgagcctcgc gtgcggacct cgtcgtcagc     540

ctggaagaag aacggcacgg caaacgcgaa catcgcgttc ttcatggcgc cgcggtcgcg     600

gcgatcgacg ctcagcgggc cgcgggtgac gcaccaccag acgtacgcgt ccttcaggcc     660

ggcgttgcgc acgaggttgt ggagaatctc cttgacctgg tcgcgattga acggattctc     720

aaggaagaac ttcgccgacg actcttccat gcgcgtgagg tgatcgtcga gccggaagaa     780

gttgccccgc gagacggtga cgacatcgta ggccgcgtcg gcatgcagga atcctgcgtc     840

gacgagcggg acggtcgctt cggtgatggg gacgtagttg ccgtcacaga aggcgctgcc     900

atcttcgtag cggggttcat gcggagcgcg agcatgcagc gggttctcgt gcatgatctg     960

ctggacttga atgattgcca t                                               981
```

<210> SEQ ID NO 42
<211> LENGTH: 326
<212> TYPE: PRT

<213> ORGANISM: Burkholderia sp.

<400> SEQUENCE: 42

```
Met Ala Ile Ile Gln Val Gln Gln Ile Met His Glu Asn Pro Leu His
1               5                   10                  15

Ala Arg Ala Pro His Glu Pro Arg Tyr Glu Asp Gly Ser Ala Phe Cys
            20                  25                  30

Asp Gly Asn Tyr Val Pro Ile Thr Glu Ala Thr Val Pro Leu Val Asp
        35                  40                  45

Ala Gly Phe Leu His Ala Asp Ala Ala Tyr Asp Val Val Thr Val Ser
    50                  55                  60

Arg Gly Asn Phe Phe Arg Leu Asp Asp His Leu Thr Arg Met Glu Glu
65                  70                  75                  80

Ser Ser Ala Lys Phe Phe Leu Glu Asn Pro Phe Asn Arg Asp Gln Val
                85                  90                  95

Lys Glu Ile Leu His Asn Leu Val Arg Asn Ala Gly Leu Lys Asp Ala
            100                 105                 110

Tyr Val Trp Trp Cys Val Thr Arg Gly Pro Leu Ser Val Asp Arg Arg
        115                 120                 125

Asp Arg Gly Ala Met Lys Asn Ala Met Phe Ala Phe Ala Val Pro Phe
    130                 135                 140

Phe Phe Gln Ala Asp Asp Glu Val Arg Thr Arg Gly Ser Asn Leu Leu
145                 150                 155                 160

Ile Ser Lys Leu Tyr Asn Arg Ile Ser Ala Lys Ala Val Asp Pro Thr
                165                 170                 175

Ala Lys Asn Phe His Trp Met Asp Met Lys Leu Ala Leu Phe Glu Ala
            180                 185                 190

Met Thr Gln Glu Lys Asp Trp Ala Val Leu Val Asp Glu Ser Asp Asn
        195                 200                 205

Leu Thr Glu Ala Ala Gly Ala Asn Val Phe Phe Ala Lys Asn Gly Glu
    210                 215                 220

Leu Tyr Thr Pro Ala Glu Gly Cys Leu Leu Gly Ile Thr Arg Gln Ser
225                 230                 235                 240

Val Phe Asp Ile Ala Ala Glu Leu Gly Ile Lys Val Asn Ile Gly Lys
                245                 250                 255

Tyr Thr Ala Thr Gln Leu Arg Glu Ala Asp Glu Ala Phe Thr Ser Ser
            260                 265                 270

Ser Ala Gly Gly Ile Met Pro Val Ser Ala Ile Asp Asp Gln Pro Leu
        275                 280                 285

Gly Asn Arg Asn Gly Pro Gly Pro Ile Ser Glu Lys Ile His Asn Leu
    290                 295                 300

Tyr Trp Glu Lys Arg Trp Ala Gly Trp His Ala Gln Pro Ala Glu Tyr
305                 310                 315                 320

Phe Ser Ser Val Pro Ala
                325
```

<210> SEQ ID NO 43
<211> LENGTH: 954
<212> TYPE: DNA
<213> ORGANISM: Burkholderia cenocepacia

<400> SEQUENCE: 43

```
tcagccgtcc gcgtagtcga ccgccaggct ccacgccgga tcgccgtgct tcgcccagta      60

cgcgtcgaac agccggcgcg tcatcggccc cggacggccg tcgccgatcg tcgcgtcgtt     120

cagccgcgtg accggcatga tgccgccggc cgtcgacgtg atgaacactt cgtccgcgtc     180
```

```
gcgcaactgt gcatcgtcga tgcgcgcagc ctgggcgtcg atgcccatcg ccgtcgccag    240

ctcgaacacc gtctgccgcg tgatgccatg cagcacgccg cgctcgggcg tccgcagccg    300

gccgtcgcgc acgacgaaca cgttgaaccc gggcccttcg gcgatgctgc cgtccgtgca    360

cttcagcagg accgactccg cgcccgcgtc atagcccttc agcagcccgg cgacgaggtc    420

cagccagtga tagttcttga tctgcggatc gaccgattcg ggcggaatgc gccgcacgtc    480

gtcgatcacg tggaggtgca gcccttcgcg caactgccgc tcgttcgcga ccgatccgta    540

cggcaccgcg aacgcgatga actggttcac cgcatcgcgc gggtcgcggc tgaaggtcgg    600

cgacacgccg cgcgtacaca gcatctcgac gtaggcgtgg cgcagccccg agcggcgcac    660

gcattcgacg aggatgtcgc gcagcgcatc gtcggtcaac ggcacgttca gccgcaaccg    720

cgcaagcgag cgcctgaatc gctcgatatg cttgtcgagg cggaagaagc ggccgttcca    780

aacatgcacg gtgtcgtacg tgacgtcgga gtgcagaaag ccccagtcga gcaccgatac    840

gcgcgcgtcg gcgatcggaa tgaagcggcc gttcatgtag gcggcgccct gcggaaacgc    900

gggcgcttcg acggatggaa tgccatgatg ggccgaacgt gtctcccgcg gcac          954
```

<210> SEQ ID NO 44
<211> LENGTH: 317
<212> TYPE: PRT
<213> ORGANISM: Burkholderia cenocepacia

<400> SEQUENCE: 44

```
Met Pro Arg Glu Thr Arg Ser Ala His His Gly Ile Pro Ser Val Glu
1               5                   10                  15

Ala Pro Ala Phe Pro Gln Gly Ala Ala Tyr Met Asn Gly Arg Phe Ile
            20                  25                  30

Pro Ile Ala Asp Ala Arg Val Ser Val Leu Asp Trp Gly Phe Leu His
        35                  40                  45

Ser Asp Val Thr Tyr Asp Thr Val His Val Trp Asn Gly Arg Phe Phe
    50                  55                  60

Arg Leu Asp Lys His Ile Glu Arg Phe Arg Arg Ser Leu Ala Arg Leu
65                  70                  75                  80

Arg Leu Asn Val Pro Leu Thr Asp Asp Ala Leu Arg Asp Ile Leu Val
                85                  90                  95

Glu Cys Val Arg Arg Ser Gly Leu Arg His Ala Tyr Val Glu Met Leu
            100                 105                 110

Cys Thr Arg Gly Val Ser Pro Thr Phe Ser Arg Asp Pro Arg Asp Ala
        115                 120                 125

Val Asn Gln Phe Ile Ala Phe Ala Val Pro Tyr Gly Ser Val Ala Asn
    130                 135                 140

Glu Arg Gln Leu Arg Glu Gly Leu His Leu His Val Ile Asp Asp Val
145                 150                 155                 160

Arg Arg Ile Pro Pro Glu Ser Val Asp Pro Gln Ile Lys Asn Tyr His
                165                 170                 175

Trp Leu Asp Leu Val Ala Gly Leu Leu Lys Gly Tyr Asp Ala Gly Ala
            180                 185                 190

Glu Ser Val Leu Leu Lys Cys Thr Asp Gly Ser Ile Ala Glu Gly Pro
        195                 200                 205

Gly Phe Asn Val Phe Val Val Arg Asp Gly Arg Leu Arg Thr Pro Glu
    210                 215                 220

Arg Gly Val Leu His Gly Ile Thr Arg Gln Thr Val Phe Glu Leu Ala
225                 230                 235                 240
```

```
Thr Ala Met Gly Ile Asp Ala Gln Ala Ala Arg Ile Asp Asp Ala Gln
                245                 250                 255

Leu Arg Asp Ala Asp Glu Val Phe Ile Thr Ser Thr Ala Gly Gly Ile
            260                 265                 270

Met Pro Val Thr Arg Leu Asn Asp Ala Thr Ile Gly Asp Gly Arg Pro
        275                 280                 285

Gly Pro Met Thr Arg Arg Leu Phe Asp Ala Tyr Trp Ala Lys His Gly
    290                 295                 300

Asp Pro Ala Trp Ser Leu Ala Val Asp Tyr Ala Asp Gly
305                 310                 315


<210> SEQ ID NO 45
<211> LENGTH: 864
<212> TYPE: DNA
<213> ORGANISM: alpha proteobacterium

<400> SEQUENCE: 45

ttaatattca actggatcac gatgtttacc ttcattgtgc agctgccaat aggcatgcat      60

tatacgtttc gacaaaggcc cgatattgcc ggaagcaatt ggtcgttcgt caattcttgt     120

aacaggcatc acgcccccgg cagtcgaggt tatgaagacc tcgtcagcgg ttttaagctt     180

gtcgacagta atgtcttgcg catgacatct aacttccaat tcttcgcaaa tgtcaaaaat     240

ggtttgccgc gtaattccca acaagacact tacgtcgggc gttgaaacca caccattggt     300

gatcgagaaa atattgaatc ctggcccttc ggacacgttg ccattaaggt caatcagagt     360

ggctgtgtct gctccacgtt cgtaggcagc ataaagccct ttgaccatat ccaaccaatg     420

gtaattcttg acggtaggat caacagagct tggtggaatg cgaacgacat ccgtgatcgc     480

cagatgcaaa ccacactcca actgttcttt gctggccact gaaccgaacg gaatggcaaa     540

agctatgaag cggttttctg catctcttgg atctcgactg aagttgggtg acgttcctct     600

tgtgcagatg aactcaacat atgcattttt gagcttggac aacgccacgc aattatgaag     660

aatttctatg atttgcgctt tggtgtaagg aattgacata tgcaaagcgt ccattccacg     720

ggaaaatcga tctaaatgat cacctaactt gaaaaatgct ccgccccata catgggcaac     780

gtcataagtc gcgtctgaat gaagaaaccc ataatccaaa acggacaatt tcgcctcatg     840

gataggtagg tactgcccat ccat                                            864


<210> SEQ ID NO 46
<211> LENGTH: 287
<212> TYPE: PRT
<213> ORGANISM: alpha proteobacterium

<400> SEQUENCE: 46

Met Asp Gly Gln Tyr Leu Pro Ile His Glu Ala Lys Leu Ser Val Leu
1               5                   10                  15

Asp Tyr Gly Phe Leu His Ser Asp Ala Thr Tyr Asp Val Ala His Val
            20                  25                  30

Trp Gly Gly Ala Phe Phe Lys Leu Gly Asp His Leu Asp Arg Phe Ser
        35                  40                  45

Arg Gly Met Asp Ala Leu His Met Ser Ile Pro Tyr Thr Lys Ala Gln
    50                  55                  60

Ile Ile Glu Ile Leu His Asn Cys Val Ala Leu Ser Lys Leu Lys Asn
65                  70                  75                  80

Ala Tyr Val Glu Phe Ile Cys Thr Arg Gly Thr Ser Pro Asn Phe Ser
                85                  90                  95

Arg Asp Pro Arg Asp Ala Glu Asn Arg Phe Ile Ala Phe Ala Ile Pro
```

-continued

```
            100                 105                 110

Phe Gly Ser Val Ala Ser Lys Glu Gln Leu Glu Cys Gly Leu His Leu
        115                 120                 125

Ala Ile Thr Asp Val Val Arg Ile Pro Pro Ser Ser Val Asp Pro Thr
    130                 135                 140

Val Lys Asn Tyr His Trp Leu Asp Met Val Lys Gly Leu Tyr Ala Ala
145                 150                 155                 160

Tyr Glu Arg Gly Ala Asp Thr Ala Thr Leu Ile Asp Leu Asn Gly Asn
                165                 170                 175

Val Ser Glu Gly Pro Gly Phe Asn Ile Phe Ser Ile Thr Asn Gly Val
            180                 185                 190

Val Ser Thr Pro Asp Val Ser Val Leu Leu Gly Ile Thr Arg Gln Thr
        195                 200                 205

Ile Phe Asp Ile Cys Glu Glu Leu Glu Val Arg Cys His Ala Gln Asp
    210                 215                 220

Ile Thr Val Asp Lys Leu Lys Thr Ala Asp Glu Val Phe Ile Thr Ser
225                 230                 235                 240

Thr Ala Gly Gly Val Met Pro Val Thr Arg Ile Asp Glu Arg Pro Ile
                245                 250                 255

Ala Ser Gly Asn Ile Gly Pro Leu Ser Lys Arg Ile Met His Ala Tyr
            260                 265                 270

Trp Gln Leu His Asn Glu Gly Lys His Arg Asp Pro Val Glu Tyr
        275                 280                 285
```

<210> SEQ ID NO 47
<211> LENGTH: 882
<212> TYPE: DNA
<213> ORGANISM: gamma proteobacterium

<400> SEQUENCE: 47

```
atgagtgacg agcccattat ctatatcaac ggtgactatc ttccactgtc tcaggcgcgg     60

gtatccccgg tggatcaggg attcctgctc ggtgatggcg tattcgatgt ggtctccgcc    120

tggaagggca acatcttcaa gctcgacgcc catctcgatc ggttctttga ctcgattcag    180

gccgcgcgac tcaatcacga catgagtcga gacgcgtgga aggaagcgat catcgaaacc    240

acgcgtcgca atggactcga cgatgcctcg attcgcttta tcgtgacccg cggcgagccc    300

aaaggggtgg ttgctgatcc ccgggatttt aaaccgacgt gcatcgtctg ggtggcgcct    360

tatatcttcc tcgcggatga ggagaaacgc cgcaatggta ttcgcctgat gattagcgcg    420

acgcggggtt tccctgctga caccctggac cctcgttaca aatgcctcga ccgcctgcat    480

tcacagctga ttcggcttga ggccctggag gcgggttatg acgatgcgct ttggctcgat    540

cattccggtc acgtgtccga gtcagcagcg agcaacctgt ttatcgtcaa gaatggtgtg    600

ttgtacaccc cttcagcagg aattctgcgc ggcattacac gggacaccat tctcgagctc    660

gcgaccgagc tggacatccc ctggaaagag cgacagctca gtgcgttcga tgtctatatc    720

gccgatgagg tcttcacctg cagcacagcg ggtggcgcgc ttccggtcag ggaggtcgca    780

ggtcgaacga ttcgcggcac aacccccggc ccgattaccc aggcaatcga caacgcgtat    840

tgggcgatgc gtgaaacaga ccggtacgcg acgccgcttt aa                       882
```

<210> SEQ ID NO 48
<211> LENGTH: 293
<212> TYPE: PRT
<213> ORGANISM: gamma proteobacterium

<400> SEQUENCE: 48

```
Met Ser Asp Glu Pro Ile Ile Tyr Ile Asn Gly Asp Tyr Leu Pro Leu
1               5                   10                  15

Ser Gln Ala Arg Val Ser Pro Val Asp Gln Gly Phe Leu Leu Gly Asp
            20                  25                  30

Gly Val Phe Asp Val Val Ser Ala Trp Lys Gly Asn Ile Phe Lys Leu
        35                  40                  45

Asp Ala His Leu Asp Arg Phe Phe Asp Ser Ile Gln Ala Ala Arg Leu
    50                  55                  60

Asn His Asp Met Ser Arg Asp Ala Trp Lys Glu Ala Ile Ile Glu Thr
65                  70                  75                  80

Thr Arg Arg Asn Gly Leu Asp Asp Ala Ser Ile Arg Phe Ile Val Thr
                85                  90                  95

Arg Gly Glu Pro Lys Gly Val Val Ala Asp Pro Arg Asp Phe Lys Pro
            100                 105                 110

Thr Cys Ile Val Trp Val Ala Pro Tyr Ile Phe Leu Ala Asp Glu Glu
        115                 120                 125

Lys Arg Arg Asn Gly Ile Arg Leu Met Ile Ser Ala Thr Arg Gly Phe
    130                 135                 140

Pro Ala Asp Thr Leu Asp Pro Arg Tyr Lys Cys Leu Asp Arg Leu His
145                 150                 155                 160

Ser Gln Leu Ile Arg Leu Glu Ala Leu Glu Ala Gly Tyr Asp Asp Ala
                165                 170                 175

Leu Trp Leu Asp His Ser Gly His Val Ser Glu Ser Ala Ala Ser Asn
            180                 185                 190

Leu Phe Ile Val Lys Asn Gly Val Leu Tyr Thr Pro Ser Ala Gly Ile
        195                 200                 205

Leu Arg Gly Ile Thr Arg Asp Thr Ile Leu Glu Leu Ala Thr Glu Leu
    210                 215                 220

Asp Ile Pro Trp Lys Glu Arg Gln Leu Ser Ala Phe Asp Val Tyr Ile
225                 230                 235                 240

Ala Asp Glu Val Phe Thr Cys Ser Thr Ala Gly Gly Ala Leu Pro Val
                245                 250                 255

Arg Glu Val Ala Gly Arg Thr Ile Arg Gly Thr Thr Pro Gly Pro Ile
            260                 265                 270

Thr Gln Ala Ile Asp Asn Ala Tyr Trp Ala Met Arg Glu Thr Asp Arg
        275                 280                 285

Tyr Ala Thr Pro Leu
    290
```

<210> SEQ ID NO 49
<211> LENGTH: 1014
<212> TYPE: DNA
<213> ORGANISM: Mycobacterium vanbaalenii

<400> SEQUENCE: 49

```
atgggcattg ataccggcac cagcaatctg gttgcagttg aaccgggtgc aattcgtgaa      60

gatacaccgg caggcagcgt tattcagtat agcgattatg aaattgatta tagcagcccg     120

tttgccggtg gtgttgcatg gattgaaggt gaatatctgc ctgcagaaga tgcaaaaatt     180

agcatttttg ataccggttt tggtcatagc gatctgacct ataccgttgc acatgtttgg     240

catggcaata tttttcgtct gggcgatcat ctggatcgtc tgctggatgg tgcacgtaaa     300

ctgcgtctgg atagcggtta taccaaagat gaactggccg atattaccaa aaaatgtgtg     360

agcctgagcc agctgcgtga aagctttgtt aatctgacca ttacccgtgg ttatggtaaa     420
```

```
cgtaaaggcg aaaaagatct gagcaaactg acccatcagg tgtatattta tgccattccg    480

tatctgtggg catttcctcc ggcagagcag atttttggca ccaccgcagt tgttccgcgt    540

catgttcgtc gtgccggtcg taataccgtt gatccgacca ttaaaaatta tcagtggggt    600

gatctgaccg cagcaagctt tgaagcaaaa gatcgtggtg cacgtaccgc aattctgatg    660

gatgccgata attgtgttgc agaaggtccg ggttttaacg tgtgcattgt gaaagatggt    720

aaactggcaa gcccgagccg taatgcactg ccgggtatta cacgtaaaac cgtgtttgaa    780

attgccggtg caatgggtat tgaagcagca ctgcgtgatg ttaccagcca tgaactgtat    840

gatgccgatg aaattatggc agttaccacc gcaggcggtg ttaccccgat taataccctg    900

gatggtgttc cgattggtga tggtgaaccg ggtccggtta ccgttgccat tcgtgatcgt    960

ttttgggcac tgatggatga acctggtccg ctgattgaag caattcagta ttaa        1014


<210> SEQ ID NO 50
<211> LENGTH: 337
<212> TYPE: PRT
<213> ORGANISM: Mycobacterium vanbaalenii

<400> SEQUENCE: 50

Met Gly Ile Asp Thr Gly Thr Ser Asn Leu Val Ala Val Glu Pro Gly
1               5                   10                  15

Ala Ile Arg Glu Asp Thr Pro Ala Gly Ser Val Ile Gln Tyr Ser Asp
            20                  25                  30

Tyr Glu Ile Asp Tyr Ser Ser Pro Phe Ala Gly Gly Val Ala Trp Ile
        35                  40                  45

Glu Gly Glu Tyr Leu Pro Ala Glu Asp Ala Lys Ile Ser Ile Phe Asp
    50                  55                  60

Thr Gly Phe Gly His Ser Asp Leu Thr Tyr Thr Val Ala His Val Trp
65                  70                  75                  80

His Gly Asn Ile Phe Arg Leu Gly Asp His Leu Asp Arg Leu Leu Asp
                85                  90                  95

Gly Ala Arg Lys Leu Arg Leu Asp Ser Gly Tyr Thr Lys Asp Glu Leu
            100                 105                 110

Ala Asp Ile Thr Lys Lys Cys Val Ser Leu Ser Gln Leu Arg Glu Ser
        115                 120                 125

Phe Val Asn Leu Thr Ile Thr Arg Gly Tyr Gly Lys Arg Lys Gly Glu
    130                 135                 140

Lys Asp Leu Ser Lys Leu Thr His Gln Val Tyr Ile Tyr Ala Ile Pro
145                 150                 155                 160

Tyr Leu Trp Ala Phe Pro Pro Ala Glu Gln Ile Phe Gly Thr Thr Ala
                165                 170                 175

Val Val Pro Arg His Val Arg Arg Ala Gly Arg Asn Thr Val Asp Pro
            180                 185                 190

Thr Ile Lys Asn Tyr Gln Trp Gly Asp Leu Thr Ala Ala Ser Phe Glu
        195                 200                 205

Ala Lys Asp Arg Gly Ala Arg Thr Ala Ile Leu Met Asp Ala Asp Asn
    210                 215                 220

Cys Val Ala Glu Gly Pro Gly Phe Asn Val Cys Ile Val Lys Asp Gly
225                 230                 235                 240

Lys Leu Ala Ser Pro Ser Arg Asn Ala Leu Pro Gly Ile Thr Arg Lys
                245                 250                 255

Thr Val Phe Glu Ile Ala Gly Ala Met Gly Ile Glu Ala Ala Leu Arg
            260                 265                 270

Asp Val Thr Ser His Glu Leu Tyr Asp Ala Asp Glu Ile Met Ala Val
```

-continued

```
        275                 280                 285

Thr Thr Ala Gly Gly Val Thr Pro Ile Asn Thr Leu Asp Gly Val Pro
    290                 295                 300

Ile Gly Asp Gly Glu Pro Gly Pro Val Thr Val Ala Ile Arg Asp Arg
305                 310                 315                 320

Phe Trp Ala Leu Met Asp Glu Pro Gly Pro Leu Ile Glu Ala Ile Gln
                325                 330                 335

Tyr
```